(12) United States Patent
Roquet et al.

(10) Patent No.: US 12,005,704 B2
(45) Date of Patent: Jun. 11, 2024

(54) PRINTER-FINISHER SYSTEM FOR DATA STORAGE IN DNA

(71) Applicant: Catalog Technologies, Inc., Boston, MA (US)

(72) Inventors: Nathaniel Roquet, Cambridge, MA (US); Hyunjun Park, Cambridge, MA (US); Swapnil P. Bhatia, Boston, MA (US); Mike Hazell, Boston, MA (US); Richard Day, Boston, MA (US); Richard Hammond, Boston, MA (US); James Brown, Boston, MA (US); Rodney Richardson, Boston, MA (US); Thomas Redman, Boston, MA (US); Devin Leake, Boston, MA (US)

(73) Assignee: CATALOG TECHNOLOGIES, INC., Boston, MA (US)

( * ) Notice: Subject to any disclaimer, the term of this patent is extended or adjusted under 35 U.S.C. 154(b) by 1154 days.

(21) Appl. No.: 16/414,752

(22) Filed: May 16, 2019

(65) Prior Publication Data
US 2019/0351673 A1 Nov. 21, 2019

Related U.S. Application Data

(60) Provisional application No. 62/809,870, filed on Feb. 25, 2019, provisional application No. 62/672,495, (Continued)

(51) Int. Cl.
*B41J 2/045* (2006.01)
*B41J 2/05* (2006.01)
(Continued)

(52) U.S. Cl.
CPC ....... *B41J 2/04505* (2013.01); *B41J 2/04526* (2013.01); *B41J 2/05* (2013.01);
(Continued)

(58) Field of Classification Search
CPC ...... B41J 2/04505; B41J 2/04526; B41J 2/05; B41J 2/1651; C12P 19/34; G01N 33/48; G06N 3/123; C12Q 1/68
See application file for complete search history.

(56) References Cited

U.S. PATENT DOCUMENTS

| 5,847,105 A | 12/1998 | Baldeschwieler et al. |
| 9,719,980 B2 | 8/2017 | Oliver |
| (Continued) | | |

FOREIGN PATENT DOCUMENTS

| EP | 1304163 | 4/2003 |
| WO | WO-2006055943 | 5/2006 |
| (Continued) | | |

OTHER PUBLICATIONS

US 11,667,940 B2, 06/2023, Nguyen et al. (withdrawn)
(Continued)

*Primary Examiner* — Thinh H Nguyen
(74) *Attorney, Agent, or Firm* — McDermott Will & Emery LLP

(57) ABSTRACT

Provided herein are systems and methods for storing digital information by assembling an identifier nucleic acid molecule from at least a first component nucleic acid molecule and a second component nucleic acid molecule. The system may include a first printhead configured to dispense a first droplet of a first solution comprising the first component nucleic acid molecule onto a coordinate on a substrate, and a second printhead configured to dispense a second droplet of a second solution comprising the second component nucleic acid molecule onto the coordinate on the substrate, such that the first and second component nucleic acid molecules are collocated on the substrate. The system may include a finisher that dispenses a reaction mix onto the coordinate on the substrate to physically link the first and second component nucleic acid molecules, provides a con- (Continued)

dition necessary to physically link the first and second component nucleic acid molecules, or both.

19 Claims, 16 Drawing Sheets

Related U.S. Application Data filed on May 16, 2018, provisional application No. 62/672,500, filed on May 16, 2018.

(51) Int. Cl.
  *B41J 2/165* (2006.01)
  *C12P 19/34* (2006.01)
  *G06N 3/123* (2023.01)
(52) U.S. Cl.
  CPC ............ *B41J 2/1652* (2013.01); *C12P 19/34* (2013.01); *G06N 3/123* (2013.01)

(56) References Cited

U.S. PATENT DOCUMENTS

| | | | |
|---|---|---|---|
| 9,914,966 | B1 | 3/2018 | Dimitrov et al. |
| 10,207,240 | B2* | 2/2019 | Jacobson ............... B82Y 30/00 |
| 10,294,516 | B2 | 5/2019 | Oliver |
| 10,784,470 | B2* | 9/2020 | Harjee ................. B41J 2/04581 |
| 11,308,055 | B2 | 4/2022 | Walder et al. |
| 11,612,873 | B2 | 3/2023 | Efcavitch et al. |
| 11,625,731 | B2 | 4/2023 | Negi et al. |
| 11,755,922 | B2 | 9/2023 | Milenkovic et al. |
| 2005/0214775 | A1 | 9/2005 | Adaskin |
| 2006/0144331 | A1* | 7/2006 | Hanafusa ........... G01N 35/1011 118/712 |
| 2007/0243634 | A1 | 10/2007 | Pamula et al. |
| 2009/0020427 | A1 | 1/2009 | Tan et al. |
| 2010/0022414 | A1 | 1/2010 | Link et al. |
| 2011/0178285 | A1 | 7/2011 | Lebl et al. |
| 2013/0116128 | A1 | 5/2013 | Shen et al. |
| 2019/0040458 | A1 | 2/2019 | Su et al. |
| 2019/0178840 | A1 | 6/2019 | Bashir et al. |
| 2019/0241951 | A1 | 8/2019 | Esfandyarpour et al. |
| 2019/0358604 | A1 | 11/2019 | Nguyen et al. |
| 2019/0362814 | A1 | 11/2019 | Roquet et al. |
| 2020/0256862 | A1 | 8/2020 | Shalek |
| 2020/0265890 | A1 | 8/2020 | Predki et al. |
| 2020/0327421 | A1 | 10/2020 | Bathe et al. |
| 2021/0146356 | A1 | 5/2021 | Agah et al. |
| 2021/0187944 | A1 | 6/2021 | Roquet et al. |
| 2021/0363570 | A1 | 11/2021 | Mok et al. |
| 2022/0042967 | A1 | 2/2022 | Brown et al. |
| 2022/0389483 | A1 | 12/2022 | Chen et al. |
| 2023/0090248 | A1 | 3/2023 | Froberg et al. |
| 2023/0125457 | A1 | 4/2023 | Chen et al. |
| 2023/0158469 | A1 | 5/2023 | Lackey et al. |
| 2023/0158503 | A1 | 5/2023 | Holden et al. |

FOREIGN PATENT DOCUMENTS

| | | |
|---|---|---|
| WO | WO-2007135354 | 11/2007 |
| WO | WO-2018057526 | 3/2018 |
| WO | WO-2018094115 | 5/2018 |
| WO | WO-2019053443 | 3/2019 |
| WO | WO-2019224544 | 11/2019 |
| WO | WO-2021108117 | 6/2021 |

OTHER PUBLICATIONS

Church, et al., "Next-Generation Digital Information Storage in DNA", Science, vol. 337, p. 1628, (2012).
Leproust, et al., "Synthesis of high-quality libraries of long (150mer) Oligonucleotides by a Novel Depurinaton Controlled Process", Nucleic Acids Research, vol. 38, No. 8, pp. 2522-2540 (Mar. 2010).
Somei, et al., "A Microfluidic Device for DNA Tile Self-assembly" Intelligent Virtual Agent, Lecture Notes in Computer Science, Springer, Berlin, Heidelberg, p. 325-335 (Jun. 6, 2005).
Yazdi, et al. "DNA-Based Storage: Trends and Methods", IEEE Transactions on Molecular, Biological and Multi-Scale Communications, IEEE, vol. 1, No. 3, p. 230-248 (Sep. 1, 2015).
Baronti, et al., "A guide to large-scale RNA sample preparation", Analytical and Bioanalytical Chemistry, Springer Berlin Heidelberg, Berlin/Heidelberg, vol. 410, No. 14, Mar. 15, 2018 pp. 3239-3252 (2018).
Belaghzal, et al., "Hi-C 2.0: An optimized Hi-C procedure for high-resolution genome-wide mapping of chromosome conformation", Methods, Academic Press, NL, vol. 123, Apr. 18, 2017 (Apr. 18, 2017), pp. 56-65, XP085136827, ISSN: 1046-2023, DOI: 10.1016/J.YMETH.2017.04.004.
Calus, et al., "NanoAmpli-Seq: A workflow for amplicon sequencing for mixed microbial communities on the nanopore sequencing platform.", bioRxiv, Jul. 4, 2018 (Jul. 4, 2018), XP055798010, DOI: 10.1101/244517 Retrieved from the Internet: URL:https://www.biorxiv.org/content/10.1101/244517v2.full.pdf [retrieved on Apr. 22, 2021].
Goldman, et a. "Supplementary Information Towards practical, high-capacity, low-maintenance information storage in synthesized DNA", Nature, vol. 494, No. 7435, Jan. 23, 2013 (Jan. 23, 2013), XP55968194, London, ISSN: 0028-0836, DOI: 10.1038/nature11875 Retrieved from the Internet: URL:https://static-content.springer.com/esm/art%3A10.1038%2Fnature11875/MediaObjects/41586_2013_BFnature11875_MOESM336_ESM.pdfl.
Goldman, et al., "Towards practical, high-capacity, low-maintenance information storage in synthesized DNA", Nature, Jan. 1, 2013.
PCT/US2022/034912 International Search Report and Written Opinion dated Oct. 19, 2022.
Lopez, et al., "DNA assembly for nanopore data storage readout", Nature Communications, vol. 10, No. 1, Jul. 3, 2019 (Jul. 3, 2019).
Pinto, et al., "Simultaneous and stoichiometric purification of hundreds of oligonucleotides", Nature Communications, vol. 9, No. 1, Jun. 25, 2018 (Jun. 25, 2018).
Wang, et al., "2C-ChIP: measuring chromatin immunoprecipitation signal from defined genomic regions with deep sequencing", BMC Genomics, vol. 20, No. 1, Feb. 28, 2019 (Feb. 28, 2019).
U.S. Appl. No. 17/197,658, filed Mar. 10, 2021.
U.S. Appl. No. 18/027,524, filed Mar. 21, 2023.
Al'Khafaji, A., et al., "High-throughput RNA isoform sequencing using programmable cDNA concatenation", bioRxiv, https://doi.org/10.1101/2021.10.01.462818; Oct. 1, 2021, 18 pgs.
Al'Khafaji, A., et al., "High-throughput RNA isoform sequencing using programmed cDNA concatenation", Nature Biotechnology, Jun. 8, 2023, 16 pgs.
Bell, et al., "Digitally encoded DNA nanostructures for multiplexed, single-molecule protein sensing with nanopores", Nat Nanotechnol. Jul. 2016;11(7):645-51.
Boskovic, et al., "DNA Structural Barcode Copying and Random Access", Small Structures, 2021, 6 pages.
Briggs et al., "Kinetics of nanopore fabrication during controlled breakdown of dielectric membranes in solution", Nanotechnology. Feb. 27, 2015;26(8) 10 pages.
Cui, M., et al., "Nonlinear manipulation and analysis of large DNA datasets", Nucleic Acids Research, vol. 50, No. 15, Aug. 10, 2022, pp. 8974-8985.
El-Sagheer, A., et al., "Click Nucleic Acid Ligation: Applications in Biology and Nanotechnology", Accounts of Chemical Research, vol. 45, No. 8, pp. 1258-1267. Dec. 12, 2011.
Jeffet, et al., "Super-Resolution Genome Mapping in Silicon Nanochannels", ACS Nano. Nov. 22, 2016;10(11):9823-9830.
Kuleshov, et al., "Audio Super-Resolution Using Neural Nets", Workshop Track, ICLR 2017, 8 pages.
Kwok, et al., "Nanopore fabrication by controlled dielectric breakdown", PLoS One. Mar. 21, 2014;9(3) 6 pages.
Leung, et al., "Mechanisms of solid-state nanopore enlargement under electrical stress", Nanotechnology. Oct. 30, 2020;31(44); 7 pages.

(56) References Cited

OTHER PUBLICATIONS

Luo, et al., "Design and Optimization of a Cyberphysical Digital-Microfluidic Biochip for the Polymerase Chain Reaction", IEEE Transactions on Computer-Aided Design of Integrated Circuits and Systems, vol. 34, No. 1 29-42; (Jan. 2015).

Molini, et al., "DeepSum: Deep neural network for Super-Resolution of Unregistered Multitemporal Images", IEEE Transactions on Geoscience and Remote Sensing, Jan. 15, 2020, 13 pages.

Mugele, et al., "Topical Review: Electrowetting from Basics to Applications", Journal of Physics: Condensed Matter; vol. 17, No. 28, 2005; 135 pages.

Nour-Eldin, H., et al., "Advancing uracil-excision based cloning towards an ideal technique for cloning PCR fragments", Nucleic Acids Research, 2006, vol. 34, No. 18, Sep. 26, 2006, 8 pgs.

Ott, et al., "BioScript: Programming Safe Chemistry on Laboratories-on-a-Chip", ACM Program Lang., vol. 2, No. OOPSLA, Article 128; Nov. 2018; 31 pages.

Papoulis, Athanasios, "Generalized sampling expansion", IEEE Transactions on Circuits and Systems, vol. 24, Issue 11, pp. 652-654, Oct. 31, 1977.

PCT/US2019/032758 International Search Report and Written Opinion dated, Nov. 7, 2019 (17 pages).

PCT/US2021/051301 International Search Report and Written Opinion dated, Dec. 20, 2021 (15 pages).

Schlecht, U., et al., "ConcatSeq: A method for increasing throughput of single molecule sequencing by concatenating short DNA fragments", Scientific Reports, Jul. 12, 2017, 10 pgs.

Unser, et al., "A generalized sampling theory without band-limiting constraints," IEEE Transactions on Circuits and Systems II: Analog and Digital Signal Processing, vol. 45, No. 8, pp. 959-969, Aug. 1998.

Verardo, D., et al., "Multiplex enzymatic synthesis of DNA with single-base resolution", Science Advances, Jul. 7, 2023 (13 pgs).

Waugh, et al., "Solid-state nanopore fabrication by automated controlled breakdown", Nat Protoc. Jan. 2020; 15(1):122-143.

Roquet, et al, "DNA-based data storage via combinatorial assembly", bioRxiv 2021.04.20.440194; doi: https://doi.org/10.1101/2021.04.20.440194, Apr. 20, 2021, (15 pgs).

\* cited by examiner

PRINTER-FINISHER SYSTEM FOR DATA STORAGE IN DNA

CROSS REFERENCE TO RELATED APPLICATIONS

This application claims priority to and the benefit of U.S. Provisional Patent Application No. 62/672,500, filed on May 16, 2018, and entitled "PRINTER-FINISHER SYSTEMS FOR DATA STORAGE IN DNA"; U.S. Provisional Patent Application 62/672,495, filed on May 16, 2018, and entitled "COMPOSITIONS AND METHODS FOR NUCLEIC ACID-BASED DATA STORAGE"; and U.S. Provisional Patent Application No. 62/809,870, filed on Feb. 25, 2019, and entitled "SYSTEM FOR DATA STORAGE IN DNA". The entire contents of the above-referenced applications are incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

To access digital data stored in nucleic acid molecules, the nucleic acid molecules may be sequenced. As such, nucleic acid digital data storage may be an ideal method for storing data that is not frequently accessed but may have a high volume of information to be stored or archived for long periods of time.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

The systems, assemblies, and methods of the present disclosure generally relate to creation of DNA molecules that store digital information. For example, component nucleic acid molecules (e.g., components) are selected and individually dispensed onto a substrate material such as a webbing. The components are printed or dispensed at the same location (e.g., coordinate) on the substrate so as to be co-located. The components are configured to self-assemble, or otherwise sort themselves in a predetermined order, to form identifier nucleic acid molecules (e.g., identifiers). Each identifier corresponds to a particular symbol (e.g., bit or series of bits), or that symbol's position (e.g., rank or address), in a string of symbols (e.g., a bitstream). To assemble the components, the system may print or dispense a reaction mix onto the same location, which causes the components to align themselves to form identifiers. The system may alternatively or additionally provide a condition necessary to physically link the components, such as a particular temperature that causes the components to align. Once formed, multiple identifiers may be combined into a pool of identifiers, where the pool is representative of at least a portion of the entire string of symbols.

Provided herein are systems and assemblies for storing digital information by assembling an identifier nucleic acid molecule from at least a first component nucleic acid molecule and a second component nucleic acid molecule. The system may include (a) a first printhead configured to dispense a first droplet of a first solution comprising the first component nucleic acid molecule onto a coordinate on a substrate; (b) a second printhead configured to dispense a second droplet of a second solution comprising the second component nucleic acid molecule onto the coordinate on the substrate, such that the first and second component nucleic acid molecules are collocated on the substrate; and (c) a finisher that dispenses a reaction mix onto the coordinate on the substrate to physically link the first and second component nucleic acid molecules, provides a condition necessary to physically link the first and second component nucleic acid molecules, or both. Generally, the first and second printheads may be part of a system including rows of any number of printheads and corresponding nozzles that print or dispense various components.

In some implementations, the identifier nucleic acid molecule is represents a position and a value of a symbol in a string of symbols. For example, each symbol in the string may have a corresponding identifier that represents the corresponding symbol position. In particular, the identifier may be created if the corresponding value of the symbol is 1, while identifiers representing symbols having value 0 may not be created. When all identifiers for symbols in the string are created, the identifier molecules for the string may be combined within a pool, such that the presence of specific identifiers within the pool represents a 1-value for corresponding symbol positions, while the absence of specific identifiers within the pool represents a 0-value for corresponding symbol positions. The alternative approach may be taken, in which identifiers may be created for corresponding symbol values of 0, while identifiers representing symbols having value 1 may not be created. In some implementations, the finisher includes a third printhead configured to dispense the reaction mix onto the coordinate on the substrate. The finisher may further comprise an incubator, a pooling system, or both. The incubator may provide a specific temperature condition or set of conditions that are needed for a reaction to proceed for assembling the components to form identifier nucleic acid molecules.

In some implementations, the finisher dispenses the reaction mix onto the coordinate before the first printhead dispenses the first droplet onto the coordinate, before the second printhead dispenses the second droplet onto the coordinate, or both. In general, the finisher may dispense the reaction mix onto the coordinate at any time, before any droplets are dispensed, after the first droplet is dispensed but before the last droplet is dispensed, or after all droplets are dispensed.

In some implementations, the system comprises at least one roller that moves the substrate past the first printhead, the second printhead, and the finisher. In some implementations, the roller provides linear movement of the substrate. In general, the roller may provide two-dimensional or three-dimensional movement of the substrate, which may pass each of the first and second printheads and the finisher only once, or multiple times. In some implementations, the roller is part of a reel-to-reel system that accomplishes the linear movement of the substrate at a constant speed.

In some implementations, the substrate forms a continuous loop of material, and the at least one roller is part of a set of rollers that causes the coordinate on the substrate to pass the first printhead, the second printhead, and the finisher multiple times. In general, it may be desirable to configure the system such that the at least one roller does not contact any of the coordinates on the substrate, to prevent any rubbing or possible contamination of the materials being dispensed on the substrate. Particularly, the substrate has a first surface upon which the first droplet, second droplet, and reaction mix are dispensed, and a second surface opposite the first surface, and the at least one roller contacts the second surface and does not contact the first surface. Alternatively, even if at least one of the rollers contacts the first surface, the roller may be grooved in a manner to avoid contacting any of the coordinates where material is dispensed.

In some implementations, the system comprises a second roller comprising at least one valley, wherein the second roller contacts the first surface such that the at least one valley aligns with the coordinate. In some implementations, the system comprises a second roller, wherein the substrate is rotated 180 degrees between the at least one roller and the second roller or in a spiral path, such that the second roller contacts the second surface and does not contact the first surface.

In some implementations, the coordinate has a diameter or spacing from other coordinates on the substrate of between 1 micrometer and 200 micrometers. In some implementations, the first and second droplets each have a volume between 1 pL and 50 pL.

In some implementations, the system comprises a register that tracks motion of the substrate in real-time to maintain alignment between coordinates of the substrate and the first and second printheads. In some implementations, the first and second solutions incorporate a dye, the system comprising a spot imager including a camera that verifies a proper dispense of the first and/or second droplets.

In some implementations, the system comprises a spot dryer that desiccates the first and second droplets on the substrate. In some implementations, the first printhead includes a first plurality of nozzles that dispense droplets of the first solution at different coordinates of the substrate. In some implementations, the first printhead includes a second plurality of nozzles that dispense droplets of a third solution at different coordinates of the substrate.

In some implementations, the system comprises a substrate. In some implementations, the substrate comprises a low binding plastic. In some implementations, the substrate comprises polyethylene terephthalate (PET) or polypropylene.

In some implementations, the first and second printheads are mounted within the system at an angle relative to motion of the substrate, wherein the angle enables overprinting on the coordinate. In some implementations, the first printhead is a MEMS thin film piezo ink jet head or a MEMS thermal ink jet head. In some implementations, the first and second printheads are positioned along a same track to dispense droplets onto the coordinate, the system comprising additional printheads that are positioned along at least one additional track to dispense droplets onto another coordinate in the corresponding track.

In some implementations, the finisher has a fixed internal temperature optimal for reaction incubation. In some implementations, the finisher has a fixed humidity level that controls the evaporation of the reaction mix during incubation. In some implementations, the finisher comprises a heater that heats the substrate before incubation to prevent condensation. In some implementations, the finisher includes a pooling system that consolidates multiple reactions from different coordinates on the substrate into a container. In some implementations, the finisher dispenses a reaction inhibitor onto the coordinate of the substrate before consolidation.

In some implementations, the container contains a pooling solution a reaction inhibitor. In some implementations, the reaction inhibitor is ethylenediaminetetraacetic acid (EDTA).

In some implementations, the system comprises a membrane that captures nucleic acids from fluid collected from the different coordinates on the substrate. In some implementations, the system comprises a scraper that removes nucleic acid from the substrate. In some implementations, the multiple reactions from different coordinates are pooled together into an emulsion that enables the multiple reactions to maintain their contents after being pooled.

In some implementations, the substrate is coated with a non-miscible liquid or oil. In some implementations, the system comprises an oil dispenser that dispenses oil on the coordinates. In some implementations, the substrate is coated or patterned with beads that bind the first and second component nucleic acid molecules. In some implementations, the system comprises a bead dispenser that dispenses beads on the coordinates.

In some implementations, the reaction mix comprises a ligase. In some implementations, the first solution, the second solution, and the reaction mix comprises an additive. In some implementations, the additive is configured to enable compatibility of the first solution with the first printhead, the second solution with the second printhead, or the reaction mix with the finisher. In some implementations, the additive mitigates evaporation of the of the first solution, the second solution, or the reaction mix. In some implementations, the additive comprises at least one of a humectant, a surfactant, and a biocide.

In some implementations, the system comprises a computer processor configured to execute instructions to operate the system. The instructions may include (1) a set of instructions for moving the substrate past the printheads, such as by controlling a set of rollers, for example, and (2) another set of instructions for specifying the times for each printhead or corresponding nozzle to dispense a solution.

In an aspect, the present disclosure provides a system for assembling a nucleic acid molecule, the system comprising: (a) a first printhead configured to dispense a first droplet of a first solution comprising a first component nucleic acid molecule onto a coordinate on a substrate; (b) a second printhead configured to dispense a second droplet of a second solution comprising a second component nucleic acid molecule onto the coordinate on the substrate, such that the first and second component: nucleic acid molecules are collocated on the substrate; and (c) a finisher that dispenses a reaction mix onto the coordinate on the substrate to physically link the first and second component nucleic acid molecules, provides a condition necessary to physically link the first and second component nucleic acid molecules, or both.

In some implementations, the finisher comprises a third printhead configured to dispense the reaction mix onto the coordinate on the substrate. The finisher may further comprise an incubator, a pooling system, or both. In general, the finisher may dispense the reaction mix at any time. Specifically, the reaction mix may be dispensed onto the coordinate before the first printhead dispenses the first droplet onto the coordinate, before the second printhead dispenses the second droplet onto the coordinate, or both.

In some implementations, the assembled nucleic acid molecules comprise gene-, peptide-, or RNA-encoding DNA. The assembled nucleic acid molecules may comprise a DNA aptamer library.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative implementations, in which the principles of the invention are utilized, and the accompanying drawings (also "Figure" and "FIG." herein), of which:

DETAILED DESCRIPTION

Definitions

Figure 1:
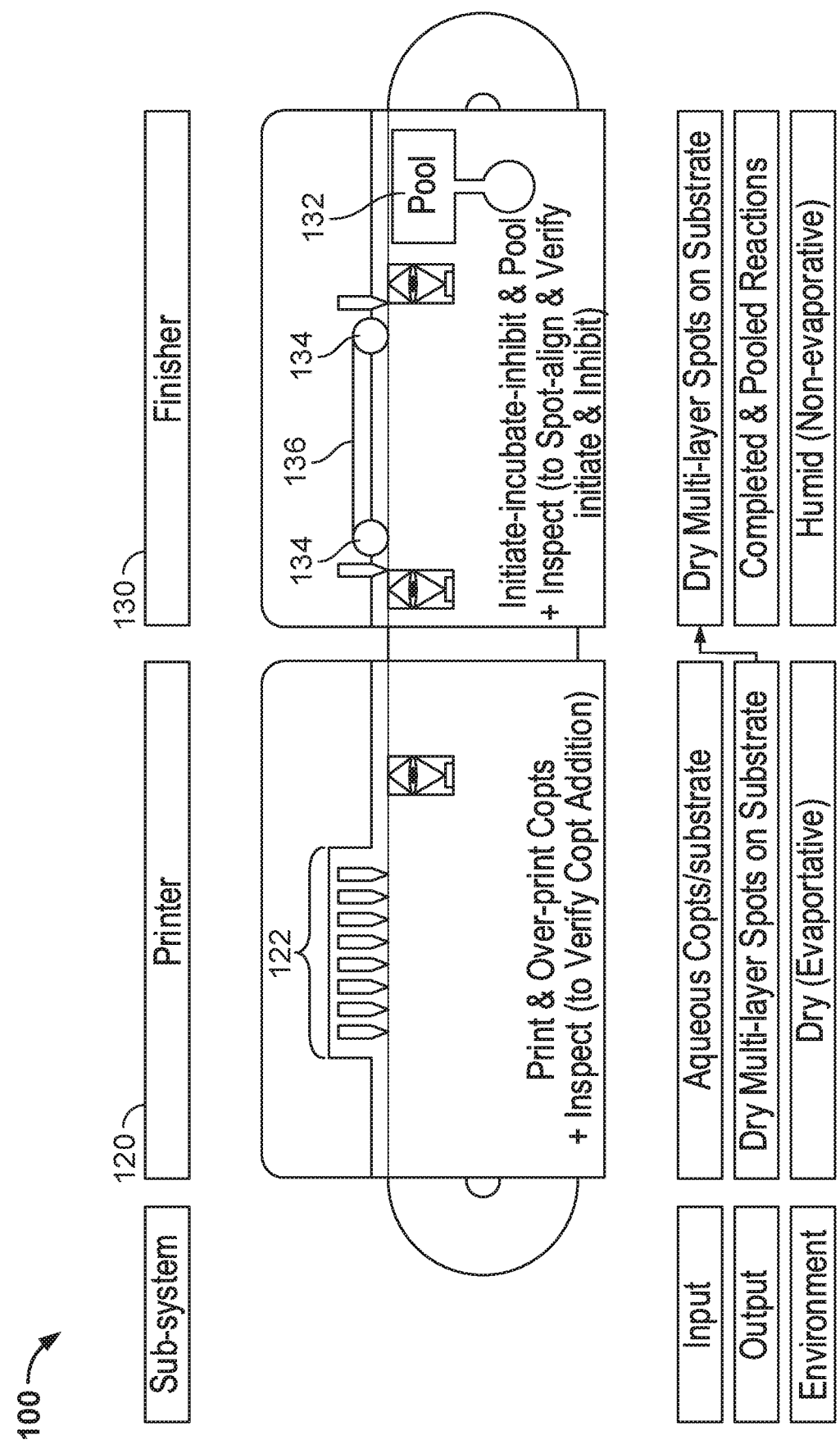
FIG. 1 illustrates an example system for storing digital information in DNA by assembling DNA identifiers from components in rapid and high throughput manner using inkjet printing. The system and its different embodiments will henceforth be referred to as the "Printer-Finisher System" or PFS.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some implementations, identifiers may comprise one or multiple concatenated components.

The term "identifier library," as used herein generally refers to a collection of identifiers corresponding to the symbols in a symbol string representing digital information. In some implementations, the absence of a given identifier in the identifier library may indicate a symbol value at a particular position. One or more identifier libraries may be combined in a pool, group, or set of identifiers. Each identifier library may include a unique barcode that identifies the identifier library.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" may refer to the alphabetical representation of a polynucleotide; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G); and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylctoysine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thioracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof.

Digital information, such as computer data, in the form of binary code can comprise a sequence or string of symbols. A binary code may encode or represent text or computer processor instructions using, for example, a binary number system having two binary symbols, typically 0 and 1, referred to as hits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of 2N unique byte-values. For example, a byte comprising 8 bits can produce a total of 28 or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Overview

Previous methods for encoding digital information into nucleic acids using inkjet printer systems have relied on base-by-base synthesis of the nucleic acids, which can be both costly and time consuming. For instance, inkjet printer based technologies have been previously used for oligo-nucleotide synthesis on a microreactor chip. However, these technologies utilize base-by-base synthesis which requires utilization of a four-step (deprotection, coupling, capping, and oxidation) solid-phase phosphoramidite cycle reaction for the addition of a single oligonucleotide during each round of synthesis. New methods described herein can encode digital information using combinatorial arrangements of components, wherein each component (e.g. nucleic acid sequence) is dispensed (e.g. printed) onto a substrate, and a reaction mixture and/or a condition is provided such that each of the components are physically linked in a single reaction.

Information can be stored in nucleic acid sequences. In some aspects of the present disclosure, provided herein are methods to encode digital information into identifiers which are built from one or more components. Each component can comprise a nucleic acid sequence. A print-based system, known as the Printer-Finisher System (or PFS), may be used to collocate and assemble components for construction of identifiers. A PFS may comprise two sub-systems, a printer and a finisher. A PFS may comprise one system, a printer which dispenses both the components and reaction mix onto a substrate. In some implementations, the two subsystems may be attached and dependent on each other for individual function. In other implementations, the two subsystems may be disjoint and capable of functioning independently.

Methods for Encoding and Writing Information to Nucleic Acid Sequence(s)

In an aspect, the present disclosure provides methods for encoding information into nucleic acid sequences. A method for encoding information into nucleic acid sequences may comprise (a) translating the information into a string of symbols, (b) mapping the string of symbols to a plurality of identifiers, and (c) constructing an identifier library comprising at least a subset of the plurality of identifiers. An individual identifier of the plurality of identifiers may comprise one or more components. An individual component of the one or more components may comprise a nucleic acid sequence. Each symbol at each position in the string of symbols may correspond to a distinct identifier. The individual identifier may correspond to an individual symbol at an individual position in the string of symbols. Moreover, one symbol at each position in the string of symbols may correspond to the absence of an identifier. For example, in a string of binary symbols (e.g., bits) of '0's and '1's, each occurrence of '0' may correspond to the absence of an identifier.

In another aspect, the present disclosure provides methods for nucleic acid-based computer data storage. A method for nucleic acid-based computer data storage may comprise (a) receiving computer data, (b) synthesizing nucleic acid molecules comprising nucleic acid sequences encoding the computer data, and (c) storing the nucleic acid molecules having the nucleic acid sequences. The computer data may be encoded in at least a subset of nucleic acid molecules synthesized and not in a sequence of each of the nucleic acid molecules.

In another aspect, the present disclosure provides methods for writing and storing information in nucleic acid sequences. The method may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides methods for nucleic acid-based computer data storage. A method for nucleic acid-based computer data storage may comprise (a) receiving computer data, (b) synthesizing a nucleic acid molecule comprising at least one nucleic acid sequence encoding the computer data, and (c) storing the nucleic acid molecule comprising the at least one nucleic acid sequence. Synthesizing the nucleic acid molecule may be in the absence of base-by-base nucleic acid synthesis.

In another aspect, the present disclosure provides methods for writing and storing information in nucleic acid sequences. A method for writing and storing information in nucleic acid sequences may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

Methods for Reading Information Stored in Nucleic Acid Sequences

In another aspect, the present disclosure provides methods for reading information encoded in nucleic acid sequences. A method for reading information encoded in nucleic acid sequences may comprise (a) providing an identifier library, (b) identifying the identifiers present in the identifier library, (c) generating a string of symbols from the identifiers present in the identifier library, and (d) compiling information from the string of symbols. An identifier library may comprise a subset of a plurality of identifiers from a combinatorial space. Each individual identifier of the subset of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied and accessed using any method described elsewhere herein.

The identifier may comprise information relating to a location of the encoded symbol, a value of the encoded symbol, or both the location and the value of the encoded symbol. An identifier may include information relating to a location of the encoded symbol and the presence or absence of the identifier in an identifier library may indicate the value of the symbol. The presence of an identifier in an identifier library may indicate a first symbol value (e.g., first bit value) in a binary string and the absence of an identifier in an identifier library may indicate a second symbol value (e.g., second bit value) in a binary string. In a binary system, basing a bit value on the presence or absence of an identifier in an identifier library may reduce the number of identifiers assembled and, therefore, reduce the write time. In an example, the presence of an identifier may indicate a bit value of '1' at the mapped location and the absence of an identifier may indicate a bit value of '0' at the mapped location.

Generating symbols (e.g., bit values) for a piece of information may include identifying the presence or absence of the identifier that the symbol (e.g., bit) may be mapped or encoded to. Determining the presence or absence of an identifier may include sequencing the present identifiers or using a hybridization array to detect the presence of an identifier. In an example, decoding and reading the encoded sequences may be performed using sequencing platforms. Examples of sequencing platforms are described in U.S. patent application Ser. No. 14/465,685 filed Aug. 21, 2014, U.S. patent application Ser. No. 13/886,234 filed May 2, 2013, and U.S. patent application Ser. No. 12/400,593 filed Mar. 9, 2009, each of which is entirely incorporated herein by reference.

In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition to, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data.

An identifier library may further comprise supplemental nucleic acid sequences that provide metadata about the information, encrypt or mask the information, or that both provide metadata and mask the information. The supplemental nucleic acids may be identified simultaneously with identification of the identifiers. Alternatively, the supplemental nucleic acids may be identified prior to or after identifying the identifiers. In an example, the supplemental nucleic acids are not identified during reading of the encoded information. The supplemental nucleic acid sequences may be indistinguishable from the identifiers. An identifier index or a key may be used to differentiate the supplemental nucleic acid molecules from the identifiers.

The efficiency of encoding and decoding data may be increased by recoding input bit strings to enable the use of fewer nucleic acid molecules. For example, if an input string is received with a high occurrence of '111' substrings, which may map to three nucleic acid molecule (e.g., identifiers) with an encoding method, it may be recoded to a '000' substring which may map to a null set of nucleic acid molecules. The alternate input substring of '000' may also be recoded to '111'. This method of recoding may reduce the total amount of nucleic acid molecules used to encode the data because there may be a reduction in the number of '1's in the dataset. In this example, the total size of the dataset may be increased to accommodate a codebook that specifies the new mapping instructions. An alternative method for increasing encoding and decoding efficiency may be to recode the input string to reduce the variable length. For example, '111' may be recoded to '00' which may shrink the size of the dataset and reduce the number of '1's in the dataset.

The speed and efficiency of decoding nucleic acid encoded data may be controlled (e.g., increased) by specifically designing identifiers for ease of detection. For example, nucleic acid sequences (e.g., identifiers) that are designed for ease of detection may include nucleic acid sequences comprising a majority of nucleotides that are easier to call and detect based on their optical, electrochemical, chemical, or physical properties. Engineered nucleic acid sequences may be either single or double stranded. Engineered nucleic acid sequences may include synthetic or unnatural nucleotides that improve the detectable properties of the nucleic acid sequence. Engineered nucleic acid sequences may comprise all natural nucleotides, all synthetic or unnatural nucleotides, or a combination of natural, synthetic, and unnatural nucleotides. Synthetic nucleotides may include nucleotide analogues such as peptide nucleic acids, locked nucleic acids, glycol nucleic acids, and threose nucleic acids. Unnatural nucleotides may include dNaM, an artificial nucleoside containing a 3-methoxy-2-naphthly group, and d5SICS, an artificial nucleoside containing a 6-methylisoquinoline-1-thione-2-yl group. Engineered nucleic acid sequences may be designed for a single enhanced property, such as enhanced optical properties, or the designed nucleic acid sequences may be designed with multiple enhanced properties, such as enhanced optical and electrochemical properties or enhanced optical and chemical properties.

Engineered nucleic acid sequences may comprise reactive natural, synthetic, and unnatural nucleotides that do not improve the optical, electrochemical, chemical, or physical properties of the nucleic acid sequences. The reactive components of the nucleic acid sequences may enable the addition of a chemical moiety that confers improved properties to the nucleic acid sequence. Each nucleic acid sequence may include a single chemical moiety or may include multiple chemical moieties. Example chemical moieties may include, but are not limited to, fluorescent moieties, chemiluminescent moieties, acidic or basic moieties, hydrophobic or hydrophilic moieties, and moieties that alter oxidation state or reactivity of the nucleic acid sequence.

A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). The sequencing platform may include the use of promiscuous reagents, increased read lengths, and the detection of specific nucleic acid sequences by the addition of detectable chemical moieties. The use of more promiscuous reagents during sequencing may increase reading efficiency by enabling faster base calling which in turn may decrease the sequencing time. The use of increased read lengths may enable longer sequences of encoded nucleic acids to be decoded per read. The addition of detectable chemical moiety tags may enable the detection of the presence or absence of a nucleic acid sequence by the presence or absence of a chemical moiety. For example, each nucleic acid sequence encoding a bit of information may be tagged with a chemical moiety that generates a unique optical, electrochemical, or chemical signal. The presence or absence of that unique optical, electrochemical, or chemical signal may indicate a '0' or a '1' bit value. The nucleic acid sequence may comprise a single chemical moiety or multiple chemical moieties. The chemical moiety may be added to the nucleic acid sequence prior to use of the nucleic acid sequence to encode data. Alternatively or in addition to, the chemical moiety may be added to the nucleic acid sequence after encoding the data, but prior to decoding the data. The chemical moiety tag may be added directly to the nucleic acid sequence or the nucleic acid sequence may comprise a synthetic or unnatural nucleotide anchor and the chemical moiety tag may be added to that anchor.

Unique codes may be applied to minimize or detect encoding and decoding errors. Encoding and decoding errors may occur from false negatives (e.g., a nucleic acid molecule or identifier not included in a random sampling). An example of an error detecting code may be a checksum sequence that counts the number of identifiers in a contiguous set of possible identifiers that is included in the identifier library. While reading the identifier library, the checksum may indicate how many identifiers from that contiguous set of identifiers to expect to retrieve, and identifiers can continue to be sampled for reading until the expected number is met. In some implementations, a checksum sequence may be included for every contiguous set of R identifiers where R can be equal in size or greater than 1, 2, 5, 10, 50, 100, 200, 500, or 1000 or less than 1000, 500, 200, 100, 50, 10, 5, or 2. The smaller the value of R, the better the error detection. In some implementations, the checksums may be supplemental nucleic acid sequences. For example, a set comprising seven nucleic acid sequences (e.g., components) may be divided into two groups, nucleic acid sequences for constructing identifiers with a product scheme (components X1-X3 in layer X and Y1-Y3 in layer Y), and nucleic acid sequences for the supplemental checksums (X4-X7 and Y4-Y7). The checksum sequences X4-X7 may indicate whether zero, one, two, or three sequences of layer X are assembled with each member of layer Y. Alternatively, the checksum sequences Y4-Y7 may indicate whether zero, one, two, or three sequences of layer Y are assembled with each member of layer X. In this example, an original identifier library with identifiers {X1Y1, X1Y3, X2Y1, X2Y2, X2Y3} may be supplemented to include checksums to become the following pool: {X1Y1, X1Y3, X2Y1, X2Y2, X2Y3, X1Y6, X2Y7, X3Y4, X6Y1, X5Y2, X6Y3}. The checksum sequences may also be used for error correction. For example, absence of X1Y1 from the above dataset and the presence of X1Y6 and X6Y1 may enable inference that the X1Y1 nucleic acid molecule is missing from the dataset. The checksum sequences may indicate whether identifiers are missing from a sampling of the identifier library or an accessed portion of the identifier library. In the case of a missing checksum sequence, access methods such as PCR or affinity tagged probe hybridization may amplify and/or isolate it. In some implementations, the checksums may not be supplemental nucleic acid sequences. They checksums may be coded directly into the information such that they are represented by identifiers.

Noise in data encoding and decoding may be reduced by constricting identifiers palindromically, for example, by using palindromic pairs of components rather than single components in the product scheme. Then the pairs of components from different layers may be assembled to one another in a palindromic manner (e.g., YXY instead of XY for components X and Y). This palindromic method may be expanded to larger numbers of layers (e.g., ZYXYZ instead of XYZ) and may enable detection of erroneous cross reactions between identifiers.

Adding supplemental nucleic acid sequences in excess (e.g., vast excess) to the identifiers may prevent sequencing from recovering the encoded identifiers. Prior to decoding the information, the identifiers may be enriched from the supplemental nucleic acid sequences. For example, the identifiers may be enriched by a nucleic acid amplification reaction using primers specific to the identifier ends. Alternatively, or in addition to, the information may be decoded without enriching the sample pool by sequencing (e.g., sequencing by synthesis) using a specific primer. In both decoding methods, it may be difficult to enrich or decode the information without having a decoding key or knowing something about the composition of the identifiers. Alternative access methods may also be employed such as using affinity tag based probes.

Systems for Encoding Binary Sequence Data

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

In an aspect, the present disclosure provides systems for encoding binary sequence data using nucleic acids. A system for encoding binary sequence data using nucleic acids may comprise a device and one or more computer processors. The device may be configured to construct an identifier library. The one or more computer processors may be individually or collectively programmed to (i) translate the information into a sting of symbols, (ii) map the string of symbols to the plurality of identifiers, and (iii) construct an identifier library comprising at least a subset of a plurality of identifiers. An individual identifier of the plurality of identifiers may correspond to an individual symbol of the string of symbols. An individual identifier of the plurality of identifiers may comprise one or more components. An individual component of the one or more components may comprise a nucleic acid sequence.

In another aspect, the present disclosure provides systems for reading binary sequence data using nucleic acids. A system for reading binary sequence data using nucleic acids may comprise a database and one or more computer processors. The database may store an identifier library encoding the information. The one or more computer processors may be individually or collectively programmed to (i) identify the identifiers in the identifier library, (ii) generate a plurality of symbols from identifiers identified in (i), and (iii) compile the information from the plurality of symbols. The identifier library may comprise a subset of a plurality of identifiers. Each individual identifier of the plurality of identifiers may correspond to an individual symbol in a string of symbols. An identifier may comprise one or more components. A component may comprise a nucleic acid sequence.

Non-limiting implementations of methods for using the system to encode digital data can comprise steps for receiving digital information in the form of byte streams. Parsing the byte streams into individual bytes, mapping the location of a bit within the byte using a nucleic acid index (or identifier rank), and encoding sequences corresponding to either bit values of 1 or bit values of 0 into identifiers. Steps for retrieving digital data can comprise sequencing a nucleic acid sample or nucleic acid pool comprising sequences of nucleic acid (e.g., identifiers) that map to one or more bits, referencing an identifier rank to confirm if the identifier is present in the nucleic acid pool and decoding the location and bit-value information for each sequence into a byte comprising a sequence of digital information.

Systems for encoding, writing, copying, accessing, reading, and decoding information encoded and written into nucleic acid molecules may be a single integrated unit or may be multiple units configured to execute one or more of the aforementioned operations. A system for encoding and writing information into nucleic acid molecules (e.g., identifiers) may include a device and one or more computer processors. The one or more computer processors may be programmed to parse the information into strings of symbols (e.g., strings of bits). The computer processor may generate an identifier rank. The computer processor may categorize the symbols into two or more categories. One category may include symbols to be represented by a presence of the corresponding identifier in the identifier library and the other category may include symbols to be represented by an absence of the corresponding identifiers in the identifier library. The computer processor may direct the device to assemble the identifiers corresponding to symbols to be represented to the presence of an identifier in the identifier library.

The device may comprise a plurality regions, sections, or partitions. The reagents and components to assemble the identifiers may be stored in one or more regions, sections, or partitions of the device. Layers may be stored in separate regions of section of the device. A layer may comprise one or more unique components. The component in one layer may be unique from the components in another layer. The regions or sections may comprise vessels and the partitions may comprise wells. Each layer may be stored in a separate vessel or partition. Each reagent or nucleic acid sequence may be stored in a separate vessel or partition. Alternatively, or in addition to, reagents may be combined to form a master mix for identifier construction. The device may transfer reagents, components, and templates from one section of the device to be combined in another section. The device may provide the conditions for completing the assembly reaction. For example, the device may provide heating, agitation, and detection of reaction progress. The constructed identifiers may be directed to undergo one or more subsequent reactions to add barcodes, common sequences, variable sequences, or tags to one or more ends of the identifiers. The identifiers may then be directed to a region or partition to generate an identifier library. One or more identifier libraries may be stored in each region, section, or individual partition of the device. The device may transfer fluid (e.g., reagents, components, templates) using pressure, vacuum, or suction.

The identifier libraries may be stored in the device or may be moved to a separate database. The database may comprise one or more identifier libraries. The database may provide conditions for long term storage of the identifier libraries (e.g., conditions to reduce degradation of identifiers). The identifier libraries may be stored in a powder, liquid, or solid form. Aqueous solutions of identifiers may be lyophilized for more stable storage. Alternatively, identifiers may be stored in the absence of oxygen (e.g. anaerobic storage conditions). The database may provide Ultra-Violet light protection, reduced temperature (e.g., refrigeration or freezing), and protection from degrading chemicals and enzymes. Prior to being transferred to a database, the identifier libraries may be lyophilized or frozen. The identifier libraries may include ethylenediaminetetraacetic acid (EDTA) to inactivate nucleases and/or a buffer to maintain the stability of the nucleic acid molecules.

The database may be coupled to, include, or be separate from a device that writes the information into identifiers, copies the information, accesses the information, or reads the information. A portion of an identifier library may be removed from the database prior to copying, accessing or reading. The device that copies the information from the database may be the same or a different device from that which writes the information. The device that copies the information may extract an aliquot of an identifier library from the device and combine that aliquot with the reagents and constituents to amplify a portion of or the entire identifier library. The device may control the temperature, pressure, and agitation of the amplification reaction. The device may comprise partitions and one or more amplification reaction may occur in the partition comprising the identifier library. The device may copy more than one pool of identifiers at a time.

The copied identifiers may be transferred from the copy device to an accessing device. The accessing device may be the same device as the copy device. The access device may comprise separate regions, sections, or partitions. The access device may have one or more columns, bead reservoirs, or magnetic regions for separating identifiers bound to affinity tags. Alternatively, or in addition to, the access device may have one or more size selection units. A size selection unit may include agarose gel electrophoresis or any other method for size selecting nucleic acid molecules. Copying and extraction may be performed in the same region of a device or in different regions of a device.

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Information storage in nucleic acid molecules may have various applications including, but not limited to, long term information storage, sensitive information storage, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Chemical Methods for Assembling Components

Reactions and methods provided herein can be used in systems described herein for assembling identifiers from one or more components. For example, different reaction mixtures for different chemical methods provided herein can be used in the finisher of the system to assemble different components.

A. Overlap Extension PCR (OEPCR) Assembly

In OEPCR, components can be assembled in a reaction comprising polymerase and dNTPs (deoxynucleotide tri phosphates comprising dATP, dTTP, dCTP, dGTP or variants or analogs thereof). Components can be single stranded or double stranded nucleic acids. Components to be assembled adjacent to each other may have complementary 3' ends, complementary 5' ends, or homology between one component's 5' end and the adjacent component's 3' end. These end regions, termed "hybridization regions", are intended to facilitate the formation of hybridized junctions between the components during OEPCR, wherein the 3' end of one input component (or its complement) is hybridized to the 3' end of its intended adjacent component (or its complement). An assembled double-stranded product is then formed by polymerase extension. This product may then be assembled to more components through subsequent hybridization and extension.

In some implementations, the OEPCR may comprise cycling between three temperatures: a melting temperature, an annealing temperature, and an extension temperature. The melting temperature is intended to turn double stranded nucleic acids into single stranded nucleic acids, as well as remove the formation of secondary structures or hybridizations within a component or between components. Typically the melting temperature is high, for example above 95 degrees Celsius. In some implementations the melting temperature may be at least 96, 97, 98, 99, 100, 101, 102, 103, 104, or at least 105 degrees Celsius. In other implementations, the melting temperature may be at most 95, 94, 93, 92, 91, or at most 90 degrees Celsius. A higher melting temperature will improve dissociation of nucleic acids and their secondary structures, but may also cause side effects such as the degradation of nucleic acids or the polymerase. Melting temperatures may be applied to the reaction for at least 1, 2, 3, 4, or at least 5 seconds, or above, such as 30 seconds, 1 minute, 2 minutes, or 3 minutes.

The annealing temperature is intended to facilitate the formation of hybridization between complementary 3' ends of intended adjacent components (or their complements). In some implementations, the annealing temperature may match the calculated melting temperature of the intended hybridized nucleic acid formation. In other implementations, the annealing temperature may be within 10 degrees Celsius or more of said melting temperature. In some implementations, the annealing temperature pray be at least 25, 30, 50, 55, 60, 65, or at least 70 degrees Celsius. The melting temperature may depend on the sequence of the intended hybridization region between components. Longer hybridization regions have higher melting temperatures, and hybridization regions with higher percent content of Guanine or Cytosine nucleotides may have higher melting temperatures. It may therefore be possible to design components for OEPCR reactions intended to assemble optimally at particular annealing temperatures. Annealing temperatures may be applied to the reaction for at least 1, 5, 10, 15, 20, 25, or at least 30 seconds, or above.

The extension temperature is intended to initiate and facilitate the nucleic acid chain elongation of hybridized 3' ends catalyzed by one or more polymerase enzymes. In some implementations, the extension temperature may be set at the temperature in which the polymerase functions optimally in terms of nucleic acid binding strength, elongation speed, elongation stability, or fidelity. In some implementations, the extension temperature may be at least 30, 40, 50, 60, or at least 70 degrees Celsius, or above. Annealing temperatures may be applied to the reaction for at least 1, 5, 10, 15, 20, 25, 30, 40, 50, or at least 60 seconds or above. Recommended extension times may be around 15 to 45 seconds per kilobase of expected elongation.

In some implementations of OEPCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some implementations, OEPCR may be performed with one temperature cycle. Such implementations may involve the intended assembly of just two components. In other implementations, OEPCR may be performed with multiple temperature cycles. Any given nucleic acid in OEPCR may only assemble to at most one other nucleic acid in one cycle. This is because assembly (or extension or elongation) may only occurs at the 3' end of a nucleic acid and each nucleic acid only has one 3' end. Therefore, the assembly of multiple components may require multiple temperature cycles. For example, assembling four components may involve 3 temperature cycles. Assembling 6 components may involve 5 temperature cycles. Assembling 10 components may involve 9 temperature cycles. In some implementations, using more temperature cycles than the minimum required may increase assembly efficiency. For example using four temperature cycles to assemble two components may yield more product than only using one temperature cycle. This is because the hybridization and elongation of components is a statistical event that occurs with a fraction of the total number of components in each cycle. So the total fraction of assembled components may increase with increased cycles.

In addition to temperature cycling considerations, the design of the nucleic acid sequences in OEPCR may influence the efficiency of their assembly to one another. Nucleic acids with long hybridization regions may hybridize more efficiently at a given annealing temperature compared with nucleic acids with short hybridization regions. This is because a longer hybridized product contains a larger number of stable base-pairs and may therefore be a more stable overall hybridized product than a shorter hybridized product. Hybridization regions may have a length of at least 1, 2, 3, 4, 5, 6, 7, 8, 9, or at least 10, or more bases.

Hybridization regions with high guanine or cytosine content may hybridize more efficiently at a given temperature than hybridization regions with low guanine or cytosine content. This is because guanine forms a more stable base-pair with cytosine than adenine does with thymine. Hybridization regions may have a guanine or cytosine content (also known as GC content) of anywhere from 0% to 100%. For example, hybridization regions may have a guanine or cytosine content from 0% to 5%, from 5% to 10%, from 10% to 15%, from 15% to 20%, from 20% to 25%, from 25% to 30%, from 30% to 35%, from 35% to 40%, from 40% to 45%, from 45% to 50%, from 50% to 55%, from 55% to 60%, from 60% to 65%, from 65% to 70%, from 70% to 75%, from 75% to 80%, from 80% to 85%, from 85% to 90%, from 90% to 95%, or from 95% to 100%.

In addition to hybridization region length and GC content, there are many more aspects of the nucleic acid sequence design that may affect the efficiency of the OEPCR. For example, the formation of undesired secondary structures within a component may interfere with its ability to form a hybridization product with its intended adjacent component. These secondary structures may include hairpin loops. The types of possible secondary structures and their stability (for example meting temperature) for a nucleic acid may be predicted based on the sequence. Design space search algorithms may be used to determine nucleic acid sequences that meet proper length and GC content criteria for efficient OEPCR, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (nucleic acid molecules that hybridize with nucleic acid molecules of the same sequence) and unwanted heterodimers (nucleic acid sequences that hybridize with other nucleic acid sequences aside from their intended assembly partner) may interfere with OEPCR. Similar to secondary structures within a nucleic acid, the formation of homodimers and heterodimers may be predicted and accounted for during nucleic acid design using computation methods and design space search algorithms.

Longer nucleic acid sequences or higher GC content may create increased formation of unwanted secondary structures, homodimers, and heterodimers with the OEPCR. Therefore, in some implementations, the use of shorter nucleic acid sequences or lower GC content may lead to higher assembly efficiency. These design principles may counteract the design strategies of using long hybridization regions or high GC content for more efficient assembly. As such, in some implementations, OEPCR may be optimized by using long hybridization regions with high GC content but short non-hybridization regions with low GC content.

The overall length of nucleic acids may be at least 10, 20, 30, 40, 50, 60, 70, 80, 90, or at least 100 bases, or above. In some implementations, there may be an optimal length and optimal GC content for the hybridization regions of nucleic acids where the assembly efficiency is optimized.

A larger number of distinct nucleic acids in an OEPCR reaction may interfere with the expected assembly efficiency. This is because a larger number of distinct nucleic acid sequences may create a higher probability for undesirable molecular interactions, particularly in the form of heterodimers. Therefore in some implementations of OEPCR that assemble large numbers of components, nucleic acid sequence constraints may become more stringent for efficient assembly.

Primers for amplifying the anticipated final assembled product may be included in an OEPCR reaction. The OEPCR reaction may then be performed with more temperature cycles to improve the yield of the assembled product, not just by creating more assemblies between the constituent components, but also by exponentially amplifying the full assembled product in the manner of conventional PCR.

Additives may be included in the OEPCR reaction to improve assembly efficiency. For example, the addition of Betaine, Dimethyl sulfoxide (DMSO), non-ionic detergents, Formamide, Magnesium, Bovine Serum Albumin (BSA), or combinations thereof. Additive content (weight per volume) may be at least 0% %, 5%, 10%, or at least 20%, or more.

Various polymerases may be used for OEPCR. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. This process is referred to as A-tailing and may be inhibitory to OEPCR as the addition of an Adenine base may disrupt the designed 3' complementarity between intended adjacent components. OEPCR may also be referred to as polymerase cycling assembly (or PCA).

B. Ligation Assembly

In ligation assembly, separate nucleic acids are assembled in a reaction comprising one or more ligase enzymes and additional co-factors. Co-factors may include Adenosine Tri-Phosphate (ATP), Dithiothreitol (DTT), or Magnesium ion (Mg2+). During ligation, the 3'-end of one nucleic acid strand is covalently linked to the 5' end of another nucleic acid strand, thus forming an assembled nucleic acid. Components in a ligation reaction may be blunt-ended double stranded DNA (dsDNA), single stranded DNA (ssDNA), or partially hybridized single-stranded DNA. Strategies that bring the ends of nucleic acids together increase the frequency of viable substrate for ligase enzymes, and thus may be used for improving the efficiency of ligase reactions. Blunt-ended dsDNA molecules tend to form hydrophobic stacks on which ligase enzymes may act, but a more successful strategy for bringing nucleic acids together may be to use nucleic acid components with either 5' or 3' single-stranded overhangs that have complementarity for the overhangs of components to which they are intended to assemble. In the latter instance, more stable nucleic acid duplexes may form due to base-base hybridization.

When a double stranded nucleic acid has an overhang strand on one end, the other strand on the same end may be referred to as a "cavity". Together, a cavity and overhang form a "sticky end", also known as a "cohesive-end". A sticky end may be either a 3' overhang and a 5' cavity, or a 5' overhang and a 3' cavity. The sticky-ends between two intended adjacent components may be designed to have complementarity such that the overhang of both sticky ends hybridize such that each overhang ends directly adjacent to the beginning of the cavity on the other component. This forms a "nick" (a double stranded DNA break) that may be "sealed" (covalently linked through a phosphodiester bond) by the action of a ligase. Either the nick on one strand or the other, or both, may be sealed. Thermodynamically, the top and bottom strand of a molecule that forms a sticky end may move between associated and dissociated states, and therefore the sticky end may be a transient formation. Once, however, the nick along one strand of a sticky end duplex between two components is sealed, that covalent linkage remains even if the members of the opposite strand dissociate. The linked strand may then become a template to which the intended adjacent members of the opposite strand can bind and once again form a nick that may be sealed.

Sticky ends may be created by digesting dsDNA with one or more endonucleases. Endonucleases (that may be referred to as restriction enzymes) may target specific sites (that may be referred to as restriction sites) on either or both ends of dsDNA molecule, and create a staggered cleavage (sometimes referred to as a digestion) thus leaving a sticky end. The digest may leave a palindromic overhang (an overhang with a sequence that is the reverse complement of itself). If so, then two components digested with the same endonuclease may form complimentary sticky ends along which they may be assembled with a ligase. The digestion and ligation may occur together in the same reaction if the endonuclease and ligase are compatible. The reaction may occur at a uniform temperature, such as 4, 10, 16, 25, or 37 degrees Celsius. Or the reaction may cycle between multiple temperatures, such as between 16 degrees Celsius and 37 degrees Celsius. Cycling between multiple temperatures may enable the digestion and ligation to each proceed at their respective optimal temperatures during different parts of the cycle.

It may be beneficial to perform the digestion and ligation in separate reactions. For example, if the desired ligases and the desired endonucleases function optimally at different conditions. Or, for example, if the ligated product forms a new restriction site for the endonuclease. In these instances, it may be better to perform the restriction digest and then the ligation separately, and perhaps it may be further beneficial to remove the restriction enzyme prior to ligation. Nucleic acids may be separated from enzymes through phenol-chloroform extraction, ethanol precipitation, magnetic bead capture, and/or silica membrane adsorption, washing, and elution. Multiple endonucleases may be used in the same reaction, though care should be taken to ensure that the endonucleases do not interfere with each other and function under similar reaction conditions. Using two endonucleases, one may create orthogonal (non-complementary) sticky ends on both ends of a dsDNA component.

Endonuclease digestion will leave sticky ends with phosphorylated 5' ends. Ligases may only function on phosphorylated 5' ends, and not on non-phosphorylated 5' ends. As such, there may not be any need for an intermediate 5' phosphorylation step in between digestion and ligation, A digested dsDNA component with a palindromic overhang on its sticky end may ligate to itself. To prevent self-ligation, it may be beneficial to dephosphorylate said dsDNA component prior to ligation.

Multiple endonucleases may target different restriction sites, but leave compatible overhangs (overhangs that are the reverse complement of each other). The product of ligation of sticky ends created with two such endonucleases may result in an assembled product that does not contain a restriction site for either endonuclease at the site of ligation. Such endonucleases form the basis of assembly methods, such as biobricks assembly, that may programmably assemble multiple components using just two endonucleases by performing repetitive digestion-ligation cycles. FIG. 20 illustrates an example of a digestion-ligation cycle using endonucleases BamHI and BglII with compatible overhangs.

In some implementations, the endonucleases used to create sticky ends may be type IIS restriction enzymes. These enzymes cleave a fixed number of bases away from their restriction sites in a particular direction, therefore the sequence of the overhangs that they generate may be customized. The overhang sequences need not be palindromic. The same type IIS restriction enzyme may be used to create multiple different sticky ends in the same reaction, or in multiple reactions. Moreover, one or multiple type IIS restriction enzymes may be used to create components with compatible overhangs in the same reaction, or in multiple reactions. The ligation site between two sticky ends generated by type IIS restriction enzymes may be designed such that it does not form a new restriction site. In addition, the type IIS restriction enzyme sites may be placed on a dsDNA such that the restriction enzyme cleaves off its own restriction site when it generates a component with a sticky end. Therefore the ligation product between multiple components generated from type IIS restriction enzymes may not contain any restriction sites.

Type IIS restriction enzymes may be mixed in a reaction together with ligase to perform the component digestion and ligation together. The temperature of the reaction may be cycled between two or more values to promote optimal digestion and ligation. For example, the digestion may be performed optimally at 37 degrees Celsius and the ligation may be performed optimally at 16 degrees Celsius. More generally, the reaction may cycle between temperature values of at least 0, 5, 10, 15, 20, 25, 30, 35, 40, 45, 50, 55, 60, or at least 65 degrees Celsius or above. A combined digestion and ligation reaction may be used to assemble at least 2, 3, 4, 5, 6, 7, 8, 9, 10, 11, 12, 13, 14, 15, 16, 17, 18, 19, or 20 components, or more. Examples of assembly reactions that leverage Type IIS restriction enzymes to create sticky ends include Golden Gate Assembly (also known as Golden Gate Cloning) or Modular Cloning (also known as MoClo).

In some implementations of ligation, exonucleases may be used to create components with sticky ends. 3' exonucleases may be used to chew back the 3' ends from dsDNA, thus creating 5' overhangs. Likewise, 5' exonucleases may be used to chew back the 5' ends from dsDNA thus creating 3' overhangs. Different exonucleases may have different properties. For example, exonucleases may differ in the direction of their nuclease activity (5' to 3' or 3' to 5'), whether or not they act on ssDNA, whether they act on phosphorylated or non-phosphorylated 5' ends, whether or not they are able to initiate on a nick, or whether or not they are able to initiate their activity on 5' cavities, 3' cavities, 5' overhangs, or 3' overhangs. Different types of exonucleases include Lambda exonuclease, RecJf, Exonuclease III, Exonuclease I, Exonuclease T, Exonuclease V, Exonuclease VIII Exonuclease VII, Nuclease BAL_31, T5 Exonuclease, and T7 Exonuclease.

Exonuclease may be used in a reaction together with ligase to assemble multiple components. The reaction may occur at a fixed temperature or cycle between multiple temperatures, each ideal for the ligase or the exonuclease, respectively. Polymerase may be included in an assembly reaction with ligase and a 5'-to-3' exonuclease. The components in such a reaction may be designed such that components intended to assemble adjacent to each other share homologous sequences on their edges. For example, a component X to be assembled with component Y may have a 3' edge sequence of the form 5'-z-3', and the component Y may have a 5' edge sequence of the form 5'-z-3', where z is any nucleic acid sequence. We refer to homologous edge sequences of such a form as 'gibson overlaps'. As the 5' exonuclease chews back the 5' end of dsDNA components with gibson overlaps it creates compatible 3' overhangs that hybridize to each other. The hybridized 3' ends may then be extended by the action of polymerase to the end of the template component, or to the point where the extended 3' overhang of one component meets the 5' cavity of the adjacent component, thereby forming a nick that may be sealed by a ligase. Such an assembly reaction where polymerase, ligase, and exonuclease re used together is often referred to as "Gibson assembly". Gibson assembly may be performed by using T5 exonuclease, Phusion polymerase, and Taq ligase, and incubating the reaction at 50 degrees Celsius. In said instance, the use of the thermophilic ligase, Taq, enables the reaction to proceed at 50 degrees Celsius, a temperature suitable for all three types of enzymes in the reaction.

The term "Gibson assembly" may generally refer to any assembly reaction involving polymerase, ligase, and exonuclease. Gibson assembly may be used to assemble at least 2, 3, 4, 5, 6, 7, 8, 9, or at least 10, or more components. Gibson assembly may occur as a one-step, isothermal reaction or as a multi-step reaction with one or more temperature incubations. For example, Gibson assembly may occur at temperatures of at least 30, 40, 50, 60, or at least 70 degrees, or more. The incubation time for a Gibson assembly may be at least 1, 5, 10, 20, 40, or at least 80 minutes.

Gibson assembly reactions may occur optimally when gibson overlaps between intended adjacent components are a certain length and have sequence features, such as sequences that avoid undesirable hybridization events such as hairpins, homodimers, or unwanted heterodimers. Generally, gibson overlaps of at least 20 bases are recommended. But Gibson overlaps may be at least 1, 2, 3, 5, 10, 20, 30, 40, 50, 60, or at least 100, or more bases in length. The GC content of a gibson overlap may be anywhere from 0% to 100%. For example, the GC content of a gibson overlap may be from 0% to 5%, from 5% to 10%, from 10% to 15%, from 15% to 20%, from 20% to 25%, from 25% to 30%, from 30% to 35%, from 35% to 40%, from 40% to 45%, from 45% to 50%, from 50% to 55%, from 55% to 60%, from 60% to 65%, from 65% to 70%, from 70% to 75%, from 75% to 80%, from 80% to 85%, from 85% to 90%, from 90% to 95%, or from 95% to 100%.

Though Gibson assembly is commonly described with a 5' exonuclease, the reaction may also occur with a 3' exonuclease. As the 3' exonuclease chews back the 3' end of dsDNA components, the polymerase counteracts the action by extending the 3' end. This dynamic process may continue until the 5' overhang (created by the exonuclease) of two components (that share a gibson overlap) hybridize and the polymerase extends the 3' end of one component far enough to meet the 5' end of its adjacent component, thus leaving a nick that may be sealed by a ligase.

In some implementations of ligation, components with sticky ends may be created synthetically, as opposed to enzymatically, by mixing together two single stranded nucleic acids, or oligos, that do not share full complementarity.

The index region and hybridization region(s) of oligos in sticky-end ligation may be designed to facilitate the proper assembly of components. Components with long overhangs may hybridize more efficiently with each other at a given annealing temperature compared with components with short overhangs. Overhangs may have a length of at least 1, 2, 3, 4, 5, 6, 7, 8, 9, 10, 15, 20, or at least 30, or more bases.

Components with overhangs that contain high guanine or cytosine content may hybridize more efficiently to their complementary component at a given temperature than components with overhangs that contain low guanine or cytosine content. This is because guanine forms a more stable base-pair with cytosine than adenine does with thymine. Overhangs may have a guanine or cytosine content (also known as GC content) of anywhere between 0% and 100%.

As with overhang sequences, the GC content and length of the index region of an oligo may also affect ligation efficiency. This is because sticky-end components may assemble more efficiently if the top and bottom strand of each component are stably bound. Therefore, index regions may be designed with higher GC content, longer sequences, and other features that promote higher melting temperatures. However, there are many more aspects of the oligo design, for both the index region and overhang sequence(s), that may affect the efficiency of the ligation assembly. For example, the formation of undesired secondary structures within a component may interfere with its ability to form an assembled product with its intended adjacent component. This may occur due to either secondary structures in the index region, in the overhang sequence, or in both. These secondary structures may include hairpin loops. The types of possible secondary structures and their stability (for example meting temperature) for an oligo may be predicted based on the sequence. Design space search algorithms may be used to determine oligo sequences that meet proper length and GC content criteria for the formation of effective components, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (oligos that hybridize with oligos of the same sequence) and unwanted heterodimers (oligos that hybridize with other oligos aside from their intended assembly partner) may interfere with ligation. Similar to secondary structures within a component, the formation of homodimers and heterodimers may be predicted and accounted for during oligo design using computation methods and design space search algorithms.

Longer oligo sequences or higher GC content may create increased formation of unwanted secondary structures, homodimers, and heterodimers within the ligation reaction. Therefore, in some implementations, the use of shorter oligos or lower GC content may lead to higher assembly efficiency. These design principles may counteract the design strategies of using long oligos or high GC content for more efficient assembly. As such, there may be an optimal length and optimal GC content for the oligos that make up each component such that the ligation assembly efficiency is optimized. The overall length of oligos to be used in ligation may be at least 10, 20, 30, 40, 50, 60, 70, 80, 90, or at least 100 bases, or above. The overall GC content of oligos to be used in ligation may be anywhere from 0% to 100%. For example, the overall GC content of oligos to be used in ligation can be from 0% to 5%, from 5% to 10%, from 10% to 15%, from 15% to 20%, from 20% to 25%, from 25% to 30%, from 30% to 35%, from 35% to 40%, from 40% to 45%, from 45% to 50%, from 50% to 55%, from 55% to 60%, from 60% to 65%, from 65% to 70%, from 70% to 75%, from 75% to 80%, from 80% to 85%, from 85% to 90%, from 90% to 95%, or from 95% to 100%.

In addition to sticky end ligation, ligation may also occur between single-stranded nucleic acids using staple (or template or bridge) strands. This method can be referred to as staple strand ligation (SSL), template directed ligation (TDL), or bridge strand ligation. In TDL, two single stranded nucleic acids hybridize adjacently onto a template, thus forming a nick that may be sealed by a ligase. The same nucleic acid design considerations for sticky end ligation also apply to TDL. Stronger hybridization between the templates and their intended complementary nucleic acid sequences may lead to increased ligation efficiency. Therefore sequence features that improve the hybridization stability (or melting temperature) on each side of the template may improve ligation efficiency. These features may include longer sequence length and higher GC content. The length of nucleic acids in TDL, including templates, may be at least 5, 10, 20, 30, 40, 50, 60, 70, 80, 90, or at least 100 bases, or above. The GC content of nucleic acids, including templates, may be anywhere from 0% to 100%, For example, the GC content of nucleic acids, including templates, can be from 0% to 5%, from 5% to 10%, from 10% to 15%, from 15% to 20%, from 20% to 25%, from 25% to 30%, from 30% to 35%, from 35% to 40%, from 40% to 45%, from 45% to 50%, from 50% to 55%, from 55% to 60%, from 60% to 65%, from 65% to 70%, from 70% to 75%, from 75% to 80%, from 80% to 85%, from 85% to 90%, from 90% to 95%, or from 95% to 100%.

In TDL, as with sticky end ligation, care may be taken to design component and template sequences that avoid unwanted nucleic acid secondary structures by using nucleic acid structure-predicting software with sequence space search algorithms. As the components in TDL may be single stranded instead of double stranded, there may be higher incidence of unwanted secondary structures (as compared to sticky end ligation) due to the exposed bases.

TDL may also be performed with blunt-ended dsDNA components. In such reactions, in order for the staple strand to properly bridge two single-stranded nucleic acids, the staple may first need to displace or partially displace the full single-stranded complements. To facilitate the TDL, reaction with dsDNA components, the dsDNA may initially be melted with incubation at a high temperature. The reaction may then be cooled thus allowing staple strands to anneal to their proper nucleic acid complements. This process may be made even more efficient by using a relatively high concentration of template compared to dsDNA components, thus enabling the templates to outcompete the proper full-length ssDNA complements for binding. Once two ssDNA strands get assembled by their template and a ligase, that assembled nucleic acid may then become a template for the opposite full-length ssDNA complements. Therefore, ligation of blunt-ended dsDNA with TDL may be improved through multiple rounds of melting (incubation at higher temperatures) and annealing (incubation at lower temperatures). This process may be referred to as Ligase Cycling Reaction, or LCR. Proper melting and annealing temperatures depend on the nucleic acid sequences. Melting and annealing temperatures may be at least 4, 10, 20, 20, 30, 40, 50, 60, 70, 80, 90, or 100 degrees Celsius. The number of temperature cycles may be at least 1, 5, 10, 15, 20, 15, 30, or more.

All ligations may be performed in fixed temperature reactions or in multi-temperature reactions. Ligation temperatures may be at least 0, 4, 10, 20, 20, 30, 40, 50, or 60 degrees Celsius or above. The optimal temperature for ligase activity may differ depending on the type of ligase. Moreover, the rate at which components adjoin or hybridize in the reaction may differ depending on their nucleic acid sequences. Higher incubation temperatures may promote faster diffusion and therefore increase the frequency with which components temporarily adjoin or hybridize. However increased temperature may also disrupt base pair bonds and therefore decrease the stability of those adjoined or hybridized component duplexes. The optimal temperature for ligation may depend on the number of nucleic acids to be assembled, the sequences of those nucleic acids, the type of ligase, as well as other factors such as reaction additives. For example, two sticky end components with 4-base complementary overhangs may be assembled faster at 4 degrees Celsius with T4 ligase than at 25 degrees Celsius with T4 ligase. But two sticky-end components with 25-base complementary overhangs may assemble faster at 25 degrees Celsius with T4 ligase than at 4 degrees Celsius with T4 ligase, and perhaps faster than ligation with 4-base overhangs at any temperature. In some implementations of ligation, it may be beneficial to heat and slowly cool the components for annealing prior to ligase addition.

Ligation may be used to assemble at least 2, 3, 4, 5, 6, 7, 8, 9, 10, 11, 12, 13, 14, 15, 16, 17, 18, 19, 20, or more nucleic acids. Ligation incubation times may be at most 30 seconds, 1 minute, 2 minutes, 5 minutes, 10 minutes, 20 minutes, 30 minutes, 1 hour, or longer. Longer incubation times may improve ligation efficiency.

Ligation may require nucleic acids with 5' phosphorylated ends. Nucleic acid components without 5' phosphorylated ends may be phosphorylated in a reaction with polynucleotide kinase, such as T4 polynucleotide kinase (or T4 PNK). Other co-factors may be present in the reaction such as ATP, magnesium ion, or DTT. Polynucleotide kinase reactions may occur at 37 degrees Celsius for 30 minutes. Polynucleotide kinase reaction to pens ores may be at least 4, 10, 20, 20, 30, 40, 50, or 60 degrees Celsius. Polynucleotide kinase reaction incubation times may be at most, 1 minute, 5 minutes, 10 minutes, 20 minutes, 30 minutes, 60 minutes, or more. Alternatively, the nucleic acid components may be synthetically (as opposed to enzymatically) designed and manufactured with a modified 5' phosphorylation. Only nucleic acids being assembled on their 5' ends may require phosphorylation. For example, templates in TDL may not be phosphorylated as they are not intended to be assembled.

Additives may be included in a ligation reaction to improve ligation efficiency. For example, the addition of Dimethyl sulfoxide (DMSO), polyethylene glycol (PEG), 1,2-Propanediol (1,2-Prd), glycerol, Tween-20 or combinations thereof. PEG6000 may be a particularly effective ligation enhancer. PEG6000 may increase ligation efficiency by acting as a crowding agent. For example, the PEG6000 may form aggregated nodules that take up space in the ligase reaction solution and bring the ligase and components to closer proximity. Additive content (weight per volume) may be at least 0%, 1%, 5%, 10%, 20%, or more.

Various ligases may be used for ligation. The ligases can be naturally occurring or synthesized. Examples of ligases include T4 DNA Ligase, T7 DNA Ligase, 13 DNA Ligase, Taq DNA Ligase, 9oNTM DNA Ligase, *E. coli* DNA Ligase, and SplintR DNA Ligase. Different ligases may be stable and function optimally at different temperatures. For example, Taq DNA Ligase is thermostable and T4 DNA Ligase is not. Moreover, different ligases have different properties. For example, T4 DNA Ligase may ligate blunt-ended dsDNA while 17 DNA Ligase may not.

Ligation may be used to attach sequencing adapters to a library of nucleic acids. For example, the ligation may be performed with common sticky ends or staples at the ends of each member of the nucleic acid library. If the sticky end or staple at one end of the nucleic acids is distinct from that of the other end, then the sequencing adapters may be ligated asymmetrically. For example, a forward sequencing adapter may be ligated to one end of the members of the nucleic acid library and a reverse sequencing adapter may be ligate to the other end of the members of the nucleic acid library. Alternatively, blunt-ended ligation may be used to attach adapters to a library of blunt-ended double-stranded nucleic acids. Fork adapters may be used to asymmetrically attach adapters to a nucleic acid library with either blunt ends or sticky ends that are equivalent at each end (such as A-tails).

Ligation may be inhibited by heat inactivation (for example incubation at 65 degrees Celsius for at least 20 minutes), addition of a denaturant, or addition of a chelator such as EDTA.

C. Restriction Digest

Restriction digests are reactions in which restriction endonucleases (or restriction enzymes) recognize their cognate restriction site on nucleic acids and subsequently cleave (or digest) the nucleic acids containing said restriction site. Type I, type II, type III, or type IV restriction enzymes may be used for restriction digests. Type II restriction enzymes may be the most efficient restriction enzymes for nucleic acid digestions. Type II restriction enzymes may recognize palindromic restriction sites and cleave nucleic acids within the recognition site. Examples of said restriction enzymes (and their restriction sites include) AatII (GACGTC), AfeI (AGCGCT), ApaI (GGGCCC), DpnI (GATC), EcoRI (GAMIC), NgeI (GCTAGC), and many more. Some restriction enzymes, such as DpnI and AfeI, may cut their restriction sites in the center, thus leaving blunt-ended dsDNA products. Other restriction enzymes, such as EcoRI and AatII, cut their restriction sites off-center, thus leaving dsDNA products with sticky ends (or staggered ends). Some restriction enzymes may target discontinuous restriction sites. For example, the restriction enzyme AlwNI recognizes the restriction site CAGNNNCTG, where N may be either A, T, C, or G. Restriction sites may be at least 2, 4, 6, 8, 10, or more bases long.

Some Type II restriction enzymes cleave nucleic acids outside of their restriction sites. The enzymes may be sub-classified as either Type IIS or Type IIG restriction enzymes. Said enzymes may recognize restriction sites that are non-palindromic. Examples of said restriction enzymes include BbsI, that recognizes GAAAC and creates a staggered cleavage 2 (same strand) and 6 (opposite strand) bases further downstream. Another example includes BsaI, that recognizes GGTCTC and creates a staggered cleavage 1 (same strand) and 5 (opposite strand) bases further downstream. Said restriction enzymes may be used for golden gate assembly or modular cloning (MoClo). Some restriction enzymes, such as BcgI (a Type IIG restriction enzyme) may create a staggered cleavage on both ends of its recognition site. Restriction enzymes may cleave nucleic acids at least 1, 5, 10, 15, 20, or more bases away from their recognition sites. Because said restriction enzymes may create staggered cleavages outside of their recognitions sites, the sequences of the resulting nucleic acid overhangs may be arbitrarily designed. This is as opposed to restriction enzymes that create staggered cleavages within their recognition sites, where the sequence of a resulting nucleic acid overhang is coupled to the sequence of the restriction site. Nucleic acid overhangs created by restriction digests may be at least 1, 2, 3, 4, 5, 6, 7, 8, or more bases long. When restriction enzymes cleave nucleic acids, the resulting 5' ends contain a phosphate.

One or more nucleic acid sequences may be included in a restriction digest reaction. Likewise, one or more restriction enzymes may be used together in a restriction digest reaction. Restriction digests may contain additives and cofactors including potassium ion, magnesium ion, sodium ion, BSA, S-Adenosyl-L-methionine (SAM), or combinations thereof. Restriction digest reactions may be incubated at 37 degrees Celsius for one hour. Restriction digest reactions may be incubated in temperatures of at least 0, 10, 20, 30, 40, 50, or 60 degrees Celsius. Optimal digest temperatures may depend on the enzymes. Restriction digest reactions may be incubated for at most 1, 10, 30, 60, 90, 120, or more minutes. Longer incubation times may result in increased digestion.

D. Nucleic Acid Amplification

Nucleic acid amplification may be executed with polymerase chain reaction, or PCR. In PCR, a starting pool of nucleic acids (referred to as the template pool or template) may be combined with polymerase, primers (short nucleic acid probes), nucleotide tri phosphates (such as dATP, dTTP, dCTP, dGTP, and analogs or variants thereof), and additional cofactors and additives such as betaine, DMSO, and magnesium ion. The template may be single stranded or double stranded nucleic acids. The primer may be a short nucleic acid sequence built synthetically to complement and hybridize to a target sequence in the template pool. Typically, there are two primers in a PCR reaction, one to complement a primer binding site on the top strand of a target template, and another to complement a primer binding site on the bottom strand of the target template downstream of the first binding site. The 5'-to-3' orientation in which these primers bind their target must be facing each other in order to successfully replicate and exponentially amplify the nucleic acid sequence in between them. Though "PCR" may typically refer to reactions specifically of said form, it may also be used more generally to refer to any nucleic acid amplification reaction.

In some implementations, PCR may comprise cycling between three temperatures: a melting temperature, an annealing temperature, and an extension temperature. The melting temperature is intended to turn double stranded nucleic acids into single stranded nucleic acids, as well as remove the formation of hybridization products and secondary structures. Typically the melting temperature is high, for example above 95 degrees Celsius. In some implementations the melting temperature may be at least 96, 97, 98, 99, 100, 101, 102, 103, 104, or 105 degrees Celsius. In other implementations the melting temperature may be at most 95, 94, 93, 92, 91, or 90 degrees Celsius. A higher melting temperature will improve dissociation of nucleic acids and their secondary structures, but may also cause side effects such as the degradation of nucleic acids or the polymerase. Melting temperatures may be applied to the reaction for at least 1, 2, 3, 4, 5 seconds, or above, such as 30 seconds, 1 minute, 2 minutes, or 3 minutes. A longer initial melting temperature step may be recommended for PCR with complex or long template.

The annealing temperature is intended to facilitate the formation of hybridization between the primers and their target to templates. In some implementations, the annealing temperature may match the calculated melting temperature of the primer. In other implementations, the annealing temperature may be within 10 degrees Celsius or more of said melting temperature. In some implementations, the annealing temperature may be at least 25, 30, 50, 55, 60, 65, or 70 degrees Celsius. The melting temperature may depend on the sequence of the primer. Longer primers may have higher melting temperatures, and primers with higher percent content of Guanine or Cytosine nucleotides may have higher melting temperatures. It may therefore be possible to design primers intended to assemble optimally at particular annealing temperatures. Annealing temperatures may be applied to the reaction for at least 1, 5, 10, 15, 20, 25, or 30 seconds, or above. To help ensure annealing, the primer concentrations may be at high or saturating amounts. Primer concentrations may be 500 nanomolar (nM). Primer concentrations may be at most 1 nM, 10 nM, 100 nM, 1000 nM, or more.

The extension temperature is intended to initiate and facilitate the 3' end nucleic acid chain elongation of primers catalyzed by one or more polymerase enzymes. In some implementations, the extension temperature may be set at the temperature in which the polymerase functions optimally in terms of nucleic acid binding strength, elongation speed, elongation stability, or fidelity. In some implementations, the extension temperature may be at least 30, 40, 50, 60, or 70 degrees Celsius, or above. Annealing temperatures may be applied to the reaction for at least 1, 5, 10, 15, 20, 25, 30, 40, 50, or 60 seconds or above. Recommended extension times may be approximately 15 to 45 seconds per kilobase of expected elongation.

In some implementations of PCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some implementations, PCR may be performed with one temperature cycle. Such implementations may involve turning targeted single stranded template nucleic into double stranded nucleic acid. In other implementations, PCR may be performed with multiple temperature cycles. If the PCR is efficient, it is expected that the number of target nucleic acid molecules will double each cycle, thereby creating an exponential increase in the number of targeted nucleic acid templates from the original template pool. The efficiency of PCR may vary. Therefore, the actual percent of targeted nucleic acid that is replicated each round may be more or less than 100%. Each PCR cycle may introduce undesirable artifacts such as mutated and recombined nucleic acids. To curtail this potential detriment, a polymerase with high fidelity and high processivity may be used. In addition, a limited number of PCR cycles may be used. PCR may involve at most 1, 5, 10, 15, 20, 25, 30, 35, 40, 45, or more cycles.

In some implementations, multiple distinct target nucleic acid sequences may amplified together in one PCR. If each target sequence has common primer binding sites, then all nucleic acid sequences may be amplified with the same set of primers. Alternatively, PCR may comprise multiple primers intended to each target distinct nucleic acids. Said PCR may be referred to as multiplex PCR. PCR may involve at most 1, 2, 3, 4, 5, 6, 7, 8, 9, 10, or more distinct primers. In PCR with multiple distinct nucleic acid targets, each PCR cycle may change the relative distribution of the targeted nucleic acids. For example, a uniform distribution may become skewed or non-uniformly distributed. To curtail this potential detriment, optimal polymerases (e.g., with high fidelity and sequence robustness) and optimal PCR conditions may be used. Factors such as annealing and extension temperature and time may be optimized. In addition, a limited number of PCR cycles may be used.

In some implementations of PCR, a primer with base mismatches to its targeted primer binding site in the template may be used to mutate the target sequence. In some implementations of PCR, a primer with an extra sequence on its 5' end (known as an overhang) may be used to attach a sequence to its targeted nucleic acid. For example, primers containing sequencing adapters on their 5' ends may be used to prepare and/or amplify a nucleic acid library for sequencing. Primers that target sequencing adapters may be used to amplify nucleic acid libraries to sufficient enrichment for certain sequencing technologies.

In some implementations, linear-PCR (or asymmetric-PCR) is used wherein primers only target one strand (not both strands) of a template. In linear-PCR the replicated nucleic acid from each cycle is not complemented to the primers, so the primers do not bind it. Therefore, the primers only replicate the original target template with each cycle, hence the linear (as opposed to exponential) amplification. Though the amplification from linear-PCR may not be as fast as conventional (exponential) PCR, the maximal yield may be greater. Theoretically, the primer concentration in linear-PCR may not become a limiting factor with increased cycles and increased yield as it would with conventional PCR. Linear-After-The-Exponential-PCR (or LATE-PCR) is a modified version of linear-PCR that may be capable of particularly high yields.

In some implementations of nucleic acid amplification, the process of melting, annealing, and extension may occur at a single temperature. Such PCR may be referred to as isothermal PCR. Isothermal PCR may leverage temperature-independent methods for dissociating or displacing the fully-complemented strands of nucleic acids from each other in favor of primer binding. Strategies include loop-mediated isothermal amplification, strand displacement amplification, helicase-dependent amplification, and nicking enzyme amplification reaction. Isothermal nucleic acid amplification may occur at temperatures of at most 20, 30, 40, 50, 60, or 70 degrees Celsius or more.

In some implementations, PCR may further comprise a fluorescent probe or dye to quantify the amount of nucleic acid in a sample. For example, the dye may interpolate into double stranded nucleic acids. An example of said dye is SYBR Green. A fluorescent probe may also be a nucleic acid sequence attached to a fluorescent unit. The fluorescent unit may be release upon hybridization of the probe to a target nucleic acid and subsequent modification from an extending polymerase unit. Examples of said probes include Taqman probes. Such probes may be used in conjunction with PCR and optical measurement tools (for excitation and detection) to quantify nucleic acid concentration in a sample. This process may be referred to as quantitative PCR (qPCR) or real-time PCR (rtPCR).

In some implementations, a PCR may be performed on single a molecule template (in a process that may be referred to as single-molecule PCR), rather than on a pool of multiple template molecules. For example, emulsion-PCR (ePCR) may be used to encapsulate single nucleic acid molecules within water droplets within an oil emulsion. The water droplets may also contain PCR reagents, and the water droplets may be held in a temperature-controlled environment capable of requisite temperature cycling for PCR. This way, multiple self-contained PCR reactions may occur simultaneously in high throughput. The stability of oil emulsions may be improved with surfactants. The movement of droplets may be controlled with pressure through microfluidic channels. Microfluidic devices may be used to create droplets, split droplets, merge droplets, inject material intro droplets, and to incubate droplets. The size of water droplets in oil emulsions may be at least 1 picoliter (pL), 10 pL, 100 pL, 1 nanoliter (nL), 10 nL, 100 nL, or more.

In some implementations, single-molecule PCR may be performed on a solid-phase substrate. Examples include the Illumina solid-phase amplification method or variants thereof. The template pool may be exposed to a solid-phase substrate, wherein the solid phase substrate may immobilize templates at a certain spatial resolution. Bridge amplification may then occur within the spatial neighborhood of each template thereby amplifying single molecules in a high throughput fashion on the substrate.

High-throughput, single-molecule PCR may be useful for amplifying a pool of distinct nucleic acids that may interfere with each other. For example, if multiple distinct nucleic acids share a common sequence region, then recombination between the nucleic acids along this common region may occur during the PCR reaction, resulting in new, recombined nucleic acids. Single-molecule PCR would prevent this potential amplification error as it compartmentalizes distinct nucleic acid sequences from each other so they may not interact. Single-molecule PCR may be particularly useful for preparing nucleic acids for sequencing. Single-molecule PCR mat also be useful for absolute quantitation of a number of targets within a template pool. For example, digital PCR (or dPCR), uses the frequency of distinct single-molecule PCR amplification signals to estimate the number of starting nucleic acid molecules in a sample.

In some implementations of PCR, a group of nucleic acids may be non-discriminantly amplified using primers for primer binding sites common to all nucleic acids. For example, primers for primer binding sites flanking all nucleic acids in a pool. Synthetic nucleic acid libraries may be created or assembled with these common sites for general amplification. However, in some implementations, PCR may be used to selectively amplify a targeted subset of nucleic acids from a pool. For example, by using primers with primer binding sites that only appear on said targeted subset of nucleic acids. Synthetic nucleic acid libraries may be created or assembled such that nucleic acids belonging to potential sub-libraries of interest all share common primer binding sites on their edges (common within the sub-library but distinct from other sub-libraries) for selective amplification of the sub-library from the more general library. In some implementations, PCR may be combined with nucleic acid assembly reactions (such as ligation or OEPCR) to selectively amplify fully assembled or potentially fully assembled nucleic acids from partially assembled or mis-assembled (or unintended or undesirable) bi-products. For example, the assembly may involve assembling a nucleic acid with a primer binding site on each edge sequence such that only a full assembled nucleic product would contain the requisite two primer binding sites for amplification. In said example, a partially assembled product may contain neither or only one of the edge sequences with the primer binding sites, and therefore should not be amplified. Likewise a mis-assembled (or unintended or undesirable) product may contain neither or only one of the edge sequences, or both edge sequences but in the incorrect orientation or separated by an incorrect amount of bases. Therefore said mis-assembled product should either not amplify or amplify to create a product of incorrect length. In the latter case the amplified mis-assembled product of incorrect length may be separated from the amplified fully assembled product of correct length by nucleic acid size selection methods, such as DNA electrophoresis in an agarose gel followed by gel extraction.

Additives may be included in the PCR to improve the efficiency of nucleic acid amplification. For example, the addition of Betaine, Dimethyl sulfoxide (DMSO), non-ionic detergents, Formamide, Magnesium, Bovine Serum Albumin (BSA), or combinations thereof. Additive content (weight per volume) may be at least 0%, 1%, 5%, 10%, 20%, or more.

Various polymerases may be used for PCR. The polymerase can be naturally occurring or synthesized. An example polymerase is a $\Phi29$ polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase $\Phi29$ (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. Additionally, some polymerases may have higher fidelity and processivity than others and may be more suitable to PCR applications, such as sequencing preparation, where it is important for the amplified nucleic acid yield to have minimal mutations and where it is important for the distribution of distinct nucleic acids to maintain uniform distribution throughout amplification.

E. Size Selection

Nucleic acids of a particular size may be selected from a sample using size-selection techniques. In some implementations, size-selection may be performed using gel electrophoresis or chromatography. Liquid samples of nucleic acids may be loaded onto one terminal of a stationary phase or gel (or matrix). A voltage difference may be placed across the gel such that the negative terminal of the gel is the terminal at which the nucleic acid samples are loaded and the positive terminal of the gel is the opposite terminal. Since the nucleic acids have a negatively charged phosphate backbone, they will migrate across the gel to the positive terminal. The size of the nucleic acid will determine its relative speed of migration through the gel. Therefore nucleic acids of different sizes will resolve on the gel as they migrate. Voltage differences may be 100V or 120V. Voltage differences may be at most 50V, 100V, 150V, 200V, 250V, or more. Larger voltage differences may increase the speed of nucleic acid migration and size resolution. However, larger voltage differences may also damage the nucleic acids or the gel. Larger voltage differences may be recommended for resolving nucleic acids of larger sizes. Typical migration times may be between 15 minutes and 60 minutes. Migration times may be at most 10 minutes, 30 minutes, 60 minutes, 90 minutes, 120 minutes, or more. Longer migration times, similar to higher voltage, may lead to better nucleic acid resolution but may lead to increased nucleic acid damage. Longer migration times may be recommended for resolving nucleic acids of larger sizes. For example, a voltage difference of 120V and a migration time of 30 minutes may be sufficient for resolving a 200-base nucleic acid from a 250-base nucleic acid.

The properties of the gel, or matrix, may affect the size-selection process. Gels typically comprise a polymer substance, such as agarose or polyacrylamide, dispersed in a conductive buffer such as TAE (Tris-acetate-EDTA) or TBE (Tris-borate-EDTA). The content (weight per volume) of the substance (e.g. agarose or acrylamide) in the gel may be at most 0.5%, 1%, 2%, 3%, 5%, 10%, 15%, 20%, 25%, or higher. Higher content may decrease migration speed. Higher content may be preferable for resolving smaller nucleic acids. Agarose gels may be better for resolving double stranded DNA (dsDNA). Polyacrylamide gels may be better for resolving single stranded DNA (ssDNA). The preferred gel composition may depend on the nucleic acid type and size, the compatibility of additives (e.g., dyes, stains, denaturing solutions, or loading buffers) as well as the anticipate downstream applications (e.g., gel extraction then ligation, PCR, or sequencing). Agarose gels may be simpler for gel extraction than polyacrylamide gels. TAE, though not as good a conductor as TBE, may also be better for gel extraction because borate (an enzyme inhibitor) carry-over in the extraction process may inhibit downstream enzymatic reactions.

Gels may further comprise a denaturing solution such as SDS (sodium dodecyl sulfate) or urea. SDS may be used, for example, to denature proteins or to separate nucleic acids from potentially bound proteins. Urea may be used to denature secondary structures in DNA. For example, urea may convert dsDNA into ssDNA, or urea may convert a folded ssDNA (for example a hairpin) to a non-folded ssDNA. Urea-polyacrylamide gels (further comprising TBE) may be used for accurately resolving ssDNA.

Samples may be incorporate into gels with different formats. In some implementations, gels may contain wells in which samples may be loaded manually. One gel may have multiple wells for running multiple nucleic acids samples. In other implementations, the gels may be attached to microfluidic channels that automatically load the nucleic acid sample(s). Each gel may be downstream of several microfluidic channels, or the gels themselves may each occupy separate microfluidic channels. The dimensions of the gel may affect the sensitivity of nucleic acid detection (or visualization). For example, thin gels or gels inside of microfluidic channels (such as in bioanalyzers or tapestations) may improve the sensitivity of nucleic acid detection. The nucleic acid detection step may be important for selecting and extracting a nucleic acid fragment of the correct size.

A ladder may be loaded into a gel for nucleic acid size reference. The ladder may contain markers of different sizes to which the nucleic acid sample may be compared. Different ladders may have different size ranges and resolutions. For example a 50 base ladder may have markers at 50, 100, 150, 200, 250, 300, 350, 400, 450, 500, 550, and 600 bases. Said ladder may be useful for detecting and selecting nucleic acids within the size range of 50 and 600 bases. The ladder may also be used as a standard for estimating the concentration of nucleic acids of different sizes in a sample.

Nucleic acid samples and ladders may be mixed with loading buffer to facilitate the gel electrophoresis (or chromatography) process. Loading buffer may contain dyes and markers to help track the migration of the nucleic acids. Loading buffer may further comprise reagents (such as glycerol) that are denser than the running buffer (e.g., TAE or TBE), to ensure that nucleic acid samples sink to the bottom of the sample loading wells (which may be submerged in the running buffer). Loading buffer may further comprise denaturing agents such as SDS or urea. Loading buffer may further comprise reagents for improving the stability of nucleic acids. For example, loading buffer may contain EDTA to protect nucleic acids from nucleases.

In some implementations, the gel may comprise a stain that binds the nucleic acid and that may be used to optically detect nucleic acids of different sizes. Stains may be specific for dsDNA, ssDNA, or both. Different stains may be compatible with different gel substances. Some stains may require excitation from a source light (or electromagnetic wave) in order to visualize. The source light may be UV (ultraviolet) or blue light. In some implementations, stains may be added to the gel prior to electrophoresis. In other implementations, stains may be added to the gel after electrophoresis. Examples of stains include Ethidium Bromide (EtBr), SYBR Safe, SYBR Gold, silver stain, or methylene blue. A reliable method for visualizing dsDNA of a certain size, for example, may be to use an agarose TAE gel with a SYBR Safe or EtBr stain. A reliable method for visualizing ssDNA of a certain size, for example, may be to use a urea-polyacrylamide TBE gel with a methylene blue or silver stain.

In some implementations, the migration of nucleic acids through gels may be driven by other methods besides electrophoresis. For example, gravity, centrifugation, vacuums, or pressure may be used to drive nucleic acids through gels so that they may resolve according to their size.

Nucleic acids of a certain size may be extracted from gels using a blade or razor to excise the band of gel containing the nucleic acid. Proper optical detection techniques and DNA ladders may be used to ensure that the excision occurs precisely at a certain band and that the excision successfully excludes nucleic acids that may belong to different, undesirable size bands. The gel band may be incubated with buffer to dissolve it, thus releasing the nucleic acids into the buffer solution. Heat or physical agitation may speed the dissolution. Alternatively, the gel band may be incubated in buffer long enough to allow diffusion of the DNA into the buffer solution without requiring gel dissolution. The buffer may then be separated from the remaining solid-phase gel, for example by aspiration or centrifugation. The nucleic acids may then be purified from the solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

As an alternative to gel excision, nucleic acids of a certain size may be separated from a by allowing them to run off the gel. Migrating nucleic acids may pass through a basin (or well) either embedded in the gel or at the end of the gel. The migration process may be timed or optically monitored such that when the nucleic acid group of a certain size enters the basin, the sample is collected from the basin. The collection may occur, for example, by aspiration. The nucleic acids may then be purified from the collected solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

Other methods for nucleic acid size selection may include mass-spectrometry or membrane-based filtration. In some implementations of membrane-based filtration, nucleic acids are passed through a membrane (for example a silica membrane) that may preferentially bind to either dsDNA, ssDNA, or both. The membrane may be designed to preferentially capture nucleic acids of at least a certain size. For example, membranes may be designed to filter out nucleic acids of less than 20, 30, 40, 50, 70, 90, or more bases. Said membrane-based, size-selection techniques may not be as stringent as gel electrophoresis or chromatography.

F. Nucleic Acid Capture

Affinity-tagged nucleic acids may be used as sequence specific probes for nucleic acid capture. The probe may be designed to complement a target sequence within a pool of nucleic acids. Subsequently, the probe may be incubated with the nucleic acid pool and hybridized to its target. The incubation temperature may be below the melting temperature of the probe to facilitate hybridization. The incubation temperature may be up to 5, 10, 15, 20, 25, or more degrees Celsius below the melting temperature of the probe. The hybridized target may be captured to a solid-phase substrate that specifically binds the affinity tag. The solid-phase substrate may be a membrane, a well, a column, or a bead. Multiple rounds of washing may remove all non-hybridized nucleic acids from the targets. The washing may occur at a temperature below the melting temperature of the probe to facilitate stable immobilization of target sequences during the wash. The washing temperature may be up to 5, 10, 15, 20, 25, or more degrees Celsius below the melting temperature of the probe. A final elution step may recover the nucleic acid targets from the solid phase-substrate, as well as from the affinity tagged probes. The elution step may occur at a temperature above the melting temperature of the probe to facilitate the release of nucleic acid targets into an elution buffer. The elution temperature may be up to 5, 10, 15, 20, 25, or more degrees Celsius above the melting temperature of the probe.

In certain implementations, the oligonucleotides bound to a solid-phase substrate may be removed from the solid-phase substrate, for example, by exposure to conditions such as acid, base, oxidation, reduction, heat, light, metal ion catalysis, displacement or elimination chemistry, or by enzymatic cleavage. In certain embodiments, the oligonucleotides may be attached to a solid support through a cleavable linkage moiety. For example, the solid support may be functionalized to provide cleavable linkers for covalent attachment to the targeted oligonucleotides. In some embodiments, the linker moiety may be of six or more atoms in length. In some embodiments, the cleavable linker may be a TOPS (two oligonucleotides per synthesis) linker, an amino linker, or a photocleavable linker.

In some implementations, biotin may be used as an affinity tag that is immobilized by streptavidin on a solid-phase substrate. Biotinylated oligonucleotides, for use as nucleic acid capture probes, may be designed and manufactured. Oligonucleotides may be biotinylated on the 5' or 3' end. They may also be biotinylated internally on thymine residues. Increased biotin on an oligo may lead to stronger capture on the streptavidin substrate. A biotin on the 3' end of an oligo may block the oligo from extending during PCR. The biotin tag may be a variant of standard biotin. For example, the biotin variant may be biotin-TEG (triethylene glycol), dual biotin, PC biotin, DesthioBiotin-TEG, and biotin Azide. Dual biotin may increase the biotin-streptavidin affinity. Biotin-TEG attaches the biotin group onto a nucleic acid separated by a TEG linker. This may prevent the biotin from interfering with the function of the nucleic acid probe, for example its hybridization to the target. A nucleic acid biotin linker may also be attached to the probe. The nucleic acid linker may comprise nucleic acid sequences that are not intended to hybridize to the target.

The biotinylated nucleic acid probe may be designed with consideration for how well it may hybridize to its target. Nucleic acid probes with higher designed melting temperatures may hybridize to their targets more strongly. Longer nucleic acid probes, as well as probes with higher GC content, may hybridize more strongly due to increased melting temperatures. Nucleic acid probes may have a length of a least 5, 10, 15, 20, 30, 40, 50, or 100 bases, or more. Nucleic acid probes may have a GC content anywhere between 0 and 100%. Care may be taken to ensure that the melting temperature of the probe does not exceed the temperature tolerance of the streptavidin substrate. Nucleic acid probes may be designed to avoid inhibitory secondary structures such as hairpins, homodimers, and heterodimers with off-target nucleic acids. There may be a tradeoff between probe melting temperature and off-target binding. There may be an optimal probe length and GC content at which melting temperature is high and off-target binding is low. A synthetic nucleic acid library may be designed such that its nucleic acids comprise efficient probe binding sites.

The solid-phase streptavidin substrate may be magnetic beads. Magnetic beads may be immobilized using a magnetic strip or plate. The magnetic strip or plate may be brought into contact with a container to immobilize the magnetic beads to the container. Conversely, the magnetic strip or plate may be removed from a container to release the magnetic beads from the container wall into a solution. Different bead properties may affect their application. Beads may have varying sizes. For example beads may be anywhere between 1 and 3 micrometers (um) in diameter. Beads may have a diameter of at most 1, 2, 3, 4, 5, 10, 15, 20, or more micrometers. Bead surfaces may be hydrophobic or hydrophilic. Beads may be coated with blocking proteins, for example BSA. Prior to use, beads may be washed or pre-treated with additives, such as blocking solution to prevent them from non-specifically binding nucleic acids.

A biotinylated probe may be coupled to the magnetic streptavidin beads prior to incubation with the nucleic acid sample pool. This process may be referred to as direct capture. Alternatively, the biotinylated probe may be incubated with the nucleic acid sample pool prior to the addition of magnetic streptavidin beads. This process may be referred to as indirect capture. The indirect capture method may improve target yield. Shorter nucleic acid probes may require a shorter amount of time to couple to the magnetic beads.

Optimal incubation of the nucleic acid probe with the nucleic acid sample may occur at a temperature that is 1 to 10 degrees Celsius or more below the melting temperature of the probe. Incubation temperatures may be at most 5, 10, 20, 30, 40, 50, 60, 70, 80, or more degrees Celsius. The recommended incubation time may be 1 hour. The incubation time may be at most 1, 5, 10, 20, 30, 60, 90, 120, or more minutes. Longer incubation times may lead to better capture efficiency. An additional 10 minutes of incubation may occur after the addition of the streptavidin beads to allow biotin-streptavidin coupling. This additional time may be at most 1, 5, 10, 20, 30, 60, 90, 120, or more minutes. Incubation may occur in buffered solution with additives such as sodium ion.

Hybridization of the probe to its target may be improved if the nucleic acid pool is single-stranded nucleic acid (as opposed to double-stranded). Preparing a ssDNA pool from a dsDNA pool may entail performing linear-PCR with one primer that commonly binds the edge of all nucleic acid sequences in the pool. If the nucleic acid pool is synthetically created or assembled, then this common primer binding site may be included in the synthetic design. The product of the linear-PCR will be ssDNA. More starting ssDNA template for the nucleic acid capture may be generated with more cycles of linear-PCR.

After the nucleic acid probes are hybridized to their targets and coupled to magnetic streptavidin beads, the beads may be immobilized by a magnet and several rounds of washing may occur. Three to five washes may be sufficient to remove non-target nucleic acids, but more or less rounds of washing may be used. Each incremental wash may further decrease non-targeted nucleic acids, but it may also decrease the yield of target nucleic acids. To facilitate proper hybridization of the target nucleic acids to the probe during the wash step, a low incubation temperature may be used. Temperatures as low as 60, 50, 40, 30, 20, 10, or 5 degrees Celsius or less may be used. The washing buffer may comprise Tris buffered solution with sodium ion.

Optimal elution of the hybridized targets from the magnetic bead-coupled probes may occur at a temperature that is equivalent to or more than the melting temperature of the probe. Higher temperatures will facilitate the dissociation of the target to the probe. Elution temperatures may be at most 30, 40, 50, 60, 70, 80, or 90 degrees Celsius, or more. Elution incubation time may be at most 1, 2, 5, 10, 30, 60 or more minutes. Typical incubation times may be approximately 5 minutes, but longer incubation times may improve yield. Elution buffer may be water or tris-buffered solution with additives such as EDTA.

Nucleic acid capture of target sequences containing at least one or more of a set of distinct sites may be performed in one reaction with multiple distinct probes for each of those sites. Nucleic acid capture of target sequences containing every member of a set of distinct sites may be performed in a series of capture reactions, one reaction for each distinct site using a probe for that particular site. The target yield after a series of capture reactions may be low, but the captured targets may subsequently be amplified with PCR. If the nucleic acid library is synthetically designed, then the targets may be designed with common primer binding sites for PCR.

Synthetic nucleic acid libraries may be created or assembled with common probe binding sites for general nucleic acid capture. These common sites may be used to selectively capture fully assembled or potentially fully assembled nucleic acids from assembly reactions, thereby filtering out partially assembled or mis-assembled (or unintended or undesirable) bi-products. For example, the assembly may involve assembling a nucleic acid with a probe binding site on each edge sequence such that only a fully assembled nucleic acid product would contain the requisite two probe binding sites necessary to pass through a series of two capture reactions using each probe. In said example, a partially assembled product may contain neither or only one of the probe sites, and therefore should not ultimately be captured. Likewise a mis-assembled (or unintended or undesirable) product may contain neither or only one of the edge sequences. Therefore said mis-assembled product may not ultimately be captured. For increased stringency, common probe binding sites may be included on each component of an assembly. A subsequent series of nucleic acid capture reactions using a probe for each component may isolate only fully assembled product (containing each component) from any bi-products of the assembly reaction. Subsequent PCR may improve target enrichment, and subsequent size-selection may improve target stringency.

In some implementations, nucleic acid capture may be used to selectively capture a targeted subset of nucleic acids from a pool. For example, by using probes with binding sites that only appear on said targeted subset of nucleic acids. Synthetic nucleic acid libraries may be created or assembled such that nucleic acids belonging to potential sub-libraries of interest all share common probe binding sites (common within the sub-library but distinct from other sub-libraries) for the selective capture of the sub-library from the more general library.

G. Lyophilization

Lyophilization is a dehydration process. Both nucleic acids and enzymes may be lyophilized. Lyophilized substances may have longer lifetimes. Additives such as chemical stabilizers may be used to maintain functional products (e.g., active enzymes) through the lyophilization process. Disaccharides, such as sucrose and trehalose, may be used as chemical stabilizers.

H. DNA Design

The sequences of nucleic acids (e.g., components) for building synthetic libraries (e.g., identifier libraries) may be designed to avoid synthesis, sequencing, and assembly complications. Moreover, they may be designed to decrease the cost of building the synthetic library and to improve the lifetime over which the synthetic library may be stored.

Nucleic acids may be designed to avoid long strings of homopolymers (or repeated base sequences) that may be difficult to synthesize. Nucleic acids may be designed to avoid homopolymers of length greater than 2, 3, 4, 5, 6, 7 or more. Moreover, nucleic acids may be designed to avoid the formation of secondary structures, such as hairpin loops, that may inhibit their synthesis process. For example, predictive software may be used to generate nucleic acid sequences that do not form stable secondary structures. Nucleic acids for building synthetic libraries may be designed to be short. Longer nucleic acids may be more difficult and expensive to synthesize. Longer nucleic acids may also have a higher chance of mutations during synthesis. Nucleic acids (e.g., components) may be at most 5, 10, 15, 20, 25, 30, 40, 50, 60 or more bases.

Nucleic acids to become components in an assembly reaction may be designed to facilitate that assembly reaction. Efficient assembly reactions typically involve hybridization between adjacent components. Sequences may be designed to promote these on-target hybridization events while avoiding potential off-target hybridizations. Nucleic acid base modifications, such as locked nucleic acids (LNAs), may be used to strengthen on-target hybridization. These modified nucleic acids may be used, for example, as staples in staple strand ligation or as sticky ends in sticky-strand ligation. Other modified bases that may be used for building synthetic nucleic acid libraries (or identifier libraries) include 2,6-Diaminopurine, 5-Bromo dU, deoxyUridine, inverted dT, inverted diDeoxy-T, Dideoxy-C, 5-Methyl dC, deoxyInosine, Super T, Super G, or 5-Nitroindole. Nucleic acids may contain one or multiple of the same or different modified bases. Some of the said modified bases are natural base analogs (for example, 5-Methyl dC and 2,6-Diaminopurine) that have higher melting temperatures and may therefore be useful for facilitating specific hybridization events in assembly reactions. Some of the said modified bases are universal bases (for example, 5-Nitroindole) that can bind to all natural bases and may therefore be useful for facilitating hybridization with nucleic acids that may have variable sequences within desirable binding sites. In addition to their beneficial roles in assembly reactions, these modified bases may be useful in primers (e.g., for PCR) and probes (e.g., for nucleic acid capture) as they may facilitate the specific binding of primers and probes to their target nucleic acids within a pool of nucleic acids.

Nucleic acids may be designed to facilitate sequencing. For example, nucleic acids may be designed to avoid typical sequencing complications such as secondary structure, stretches of homopolymers, repetitive sequences, and sequences with too high or too low of a GC content. Certain sequencers or sequencing methods may be error prone. Nucleic acid sequences (or components) that make up synthetic libraries (e.g., identifier libraries) may be designed with certain hamming distances from each other. This way, even when base resolution errors occur at a high rate in sequencing, the stretches of error-containing sequences may still be mapped back to their most likely nucleic acid (or component). Nucleic acid sequences may be designed with hamming distances of at least 1, 2, 3, 4, 5, 6, 7, 8, 9, 10, 11, 12, 13, 14, 15 or more base mutations. Alternative distance metrics from hamming distance may also be used to define a minimum requisite distance between designed nucleic acids.

Some sequencing methods and instruments may require input nucleic acids to contain particular sequences, such as adapter sequences or primer-binding sites. These sequences may be referred to as "method-specific sequences". Typical preparatory workflows for said sequencing instruments and methods may involve assembling the method-specific sequences to the nucleic acid libraries. However, if it is known ahead of time that a synthetic nucleic acid library (e.g., identifier library) will be sequenced with a particular instrument or method, then these method-specific sequences may be designed into the nucleic acids (e.g., components) that comprise the library (e.g., identifier library). For example, sequencing adapters may be assembled onto the members of a synthetic nucleic acid library in the same reaction step as when the members of a synthetic nucleic acid library are themselves assembled from individual nucleic acid components.

Nucleic acids may be designed to avoid sequences that may facilitate DNA damage. For example, sequences containing sites for site-specific nucleases may be avoided. As another example, UVB (ultraviolet-B) light may cause adjacent thymines to form pyrimidine dimers which may then inhibit sequencing and PCR. Therefore, if a synthetic nucleic acid library is intended to be stored in an environment exposed to UVB, then it may be beneficial to design its nucleic acid sequences to avoid adjacent thymines (i.e., TT).

System for Building Identifier Library

As described previously, a print-based system, known as the Printer-Finisher System (or PFS), may be used to collocate and assemble components for construction of identifiers.

Provided herein are systems for assembling an identifier from one or more components for storing information, comprising: (a) a printer for dispensing one or more components onto a substrate, wherein each of the one or more components comprises a nucleic acid sequence; and (b) a finisher for assembling said one or more components on said substrate, wherein said finisher provides a reaction mixture and/or a condition necessary for physically linking one or more nucleic acid sequences.

In some implementations, said printer further comprises a plurality of printheads, wherein each printhead of said plurality comprises one or more components. In some implementations, said printer comprises 1, 2, 3, 4, 5, 6, 7, 8, 9, 10, 11, 12, 13, 14, 15, 16, 17, 18, 19, 20, or more printheads. In some implementations, each printhead of said plurality comprises a different component. In some implementations, each printhead comprises at least one nozzle. In some implementations, each printhead comprises a row of nozzles. In some embodiments, each printhead comprises at least 1, 2, 3, 4, or more rows of nozzles. In some implementations, a printhead may be considered a set of nozzles each dispensing the same ink. In some embodiments, the row of nozzles dispenses the same ink. In some implementations, a particular subset of nozzles in a row of nozzles dispense different ink from the other nozzles in said row of nozzles. In some implementations, the row of nozzles comprises at least 20, 40, 60, 80, 100, 150, 200, 250, 300, 350, 400, or more nozzles. In some embodiments, some or all of the nozzles in a row of nozzles may be disjoint. In some implementations, said printhead dispenses a droplet comprising said component onto said substrate. In some implementations, said printhead dispenses a droplet comprises a reaction mix onto said substrate. In some implementations, said droplet is at least 1, 2, 3, 4, 5, 6, 7, 8, 9, or 10 picoliter in volume. In some implementations, said droplet is at least 10, 20, 30, 40, 50, 60, 70, or 80 picoliter in volume. In some implementations, said printer further comprises a printer base. In some implementations, said printer further comprises a register, a spot imager, and/or a spot dryer. In some implementations, said one or more components is in solution. In some implementations, said one or more components is a dry component. In some implementations, said reaction mixture comprises a ligase. The ligase can be used to ligate different components comprising nucleic acid sequences. In some implementations, said condition is a temperature condition. In some implementations, said substrate is passed through said printer and/or said finisher with linear movement. In some implementations, said linear movement is controlled by a reel-to-reel system. In some implementations, said spot imager is a camera. In some implementations, said one or more component further comprises a dye. In some implementations, said reaction mix comprises a dye. The dye can be any nucleic acid dye. The dye can be a visible dye.

In some implementations, said substrate further comprises a polymeric material. In some implementations, said printhead is a MEMS (micro-electro-mechanical systems) thin film piezo ink jet head or a MEMS thermal ink jet head. In some implementations, said one or more components comprises an additive. In some implementations, additive provides compatibility of said one or more component with said printhead. In some implementations, additive is a solute, a humectant, or a surfactant. In some implementations, said spot imager uses a line scan inspection principle. In some implementations, said finisher further comprises a finisher base.

In some implementations, said finisher further comprises a spot humidifier, a spot imager, and/or a pooling subsystem. In some implementations, said finisher further comprises a printhead. In some implementations, printhead of said finisher dispenses a volume having at least 1 pL, 5 pL, 10 pL, 50 pL, 100 pL, or 200 pL. In some implementations, said finisher comprises a fixed internal temperature that is optimal for reaction incubation. In some implementations, said finisher comprises a loop of rollers.

Printer Base System

The PFS may involve the use of one or more printheads, each capable of printing one or more nucleic acid molecules onto a substrate. Given an identifier library to be generated, the task of assembling all the identifiers that encode a given bitstream may be divided into subtasks where each subtask comprises generating a portion of the identifier library. This portion can be called a "sector" of the identifier library. The size of the sector may be chosen such that any errors in the generation of a sector by the PFS may be detected or corrected by the PFS. Errors may be caused by several sources including but not limited to a malfunctioning printhead, unintended mixing of components during or after printing, variation in the volume of reagents or nucleic acids dispensed by a printhead, misalignment between a printhead and the target coordinate (or spot) on the substrate, or drying or wetting due to high or low humidity. Some of these causes may lead to errors in which one or more identifiers to be generated are not generated. This type of error can be called a missing identifier error.

Depending on the cause, some missing identifier errors may be detected by the PFS. For example, the PFS may automatically inspect all or a portion of a printed sector using one or more cameras. The PFS may continually or at programmable intervals capture one or more images of each printed sector and subject those images to computational processing to detect whether each reaction specified has been printed on the substrate. In another embodiment, the PFS may continually or at programmable intervals monitor one or more nozzles on one or more printheads and capture images or video of the nozzles as they print a reaction to the substrate. The PFS may subject the video or images captured to image processing to detect whether all intended reagents and nucleic acid droplets were delivered to a reaction. The monitoring cameras may use visible light or light in other frequency bands. In another embodiment, the PFS may periodically print one or more test patterns from all nozzles on all printheads in a test area of the substrate. The PFS may visually capture or analyze the result of the test pattern printing with a spot imager or a camera or some other device with output amenable to analysis. In another embodiment, the PFS may print a test pattern and analyze it using one or more chemical methods of verification such as gel electrophoresis, for example.

After visual analysis, if the PFS concludes that some or all the components needed to assemble all the specified identifiers were not printed into reactions, then the PFS may report this conclusion to an error log. The control software controlling the PFS may analyze this log, either continually during printing or later, and choose to re-print sectors that contained such missing identifier errors. From the log, the control software may identify malfunctioning printheads or nozzles and print the remaining sectors using spare printheads or nozzles. In one embodiment, the control software may also exclude sectors with missing identifier errors from downstream processing steps so that such incomplete sectors are not included in the final identifier library.

The identifier library to be assembled is specified and transmitted to the PFS via a set of specification files. The identifier library to be generated may be specified in a set of smaller units called blocks. The specification files comprise a write specification file containing the scheme to be used to assemble the identifier library from DNA components, a list of scheme-specific parameters, and a list of block specification file names. A block specification may comprise a block metadata file and a block data file. A block metadata file describes information about a block such as its length, hash, and other constructer-defined parameters. A block data file specifies the set of identifiers to be generated by the PFS. The block data file may be compressed using a data compression algorithm. The identifiers comprising a block may be specified in the form of a serialized data structure such as, but not limited to, a tree, a trie, a list, or a bitmap.

For example, an identifier library to be generated using the product scheme may be specified with a block metadata file containing the component library partition scheme, and a list of names of the possible components to be used in each layer. The block data file may contain the identifiers to be generated organized as a serialized trie data structure in which each path from the root to the leaf of the trie represents an identifier and each node along the path specifies the component name to be used in that layer of that identifier. The block data file may comprise a serialization of this trie by traversing it in order starting with the root, and visiting the left child node of each node, before visiting the node itself, and then visiting its right child node.

The PFS may monitor an input queue for incoming specification files. Upon detecting a new specification, the PFS may read the write specification and program itself with the necessary component supplied to the appropriate printheads or nozzles. The PFS may read the block metadata and data files, and process them to generate print instructions for printheads. The PFS may send these instructions for each block to the printheads and obtain status information for each sector from the printheads. Sectors that failed to print correctly or completely may be reported into a log and may be automatically reprinted.

Exemplary PFS

FIG. 1 illustrates a system for storing digital information in DNA by assembling DNA identifiers from components in rapid and high throughput manner using inkjet printing, for example, thermal inkjet printing, bubble inkjet printing, and piezo-electric inkjet printing. The system and its different implementations, henceforth referred to as the "Printer-Finisher System" or PFS, can comprise two sub-systems, a printer 120 and a finisher 130. In some implementations, the two subsystems 120, 130 may be attached and dependent on each other for individual function. In other implementations, the two subsystems 120, 130 may be disjoint and capable of functioning independently.

The printer 120 comprises rows of printheads 122, each containing DNA components (or copts) in solution, or in some implementations, dried DNA components. We may refer to each aqueous solution of distinct DNA component as an "ink" or a "color". The printheads 122 may programmably (in an on-demand manner) dispense pL-scale droplets onto coordinates of a substrate (or web, or webbing). The coordinates may be at 1 micrometer (um) in diameter/spacing, 10 um in diameter/spacing, 50 um in diameter/spacing, 100 um in diameter/spacing, 150 um in diameter/spacing, 200 um in diameter/spacing or more. Inputs to printer system 120 include aqueous components/substrate. Outputs from printer system 120 include dry multi-layer spots on substrate. The environment of printer 120 may be dry (evaporative).

The finisher 130 comprises an instrument part (e.g. printhead) for dispensing reaction mix (e.g. ligase mix) for assembling components into identifiers. Inputs to finisher system 130. The finisher 130 may dispense reaction mix onto each coordinate of a substrate (or web, or webbing). The finisher 130 may then incubate the reactions, thus enabling assembly, prior to consolidating the assembled identifiers from the substrate into a single pool 132. In some implementations, the reaction mix may be dispensed as part of the printer, not the finisher. In other implementations, the reaction mix may be dispensed to each coordinate prior to the DNA components. In some embodiments, a visible dye may be incorporated into the reaction mixture.

A substrate (or web) 136 may be automatically passed through the printer and finisher with linear (one-dimensional) movement. Linear movement at a constant speed may be accomplished with a reel-to-reel system (roller to roller) 134. In some implementations, linear movement at a constant speed may be accomplished with a recirculating, or continuous, webbing. In some embodiments, linear movement at a constant speed may be accomplished using webbing following a snail path. See, e.g., FIG. 7. In some implementations, linear movement at a constant speed may be accomplished using webbing following a spiral path. In some implementations, linear movement at a constant speed may be accomplished using webbing following a 180° twist path. For instance, the webbing will undergo a 180° turn at each roller with the system, wherein the webbing will pass all rollers right-side up. In other implementations, the substrate may be fixed and the printheads may move over the substrate in two dimensions (for example in a raster pattern).

Figure 2:
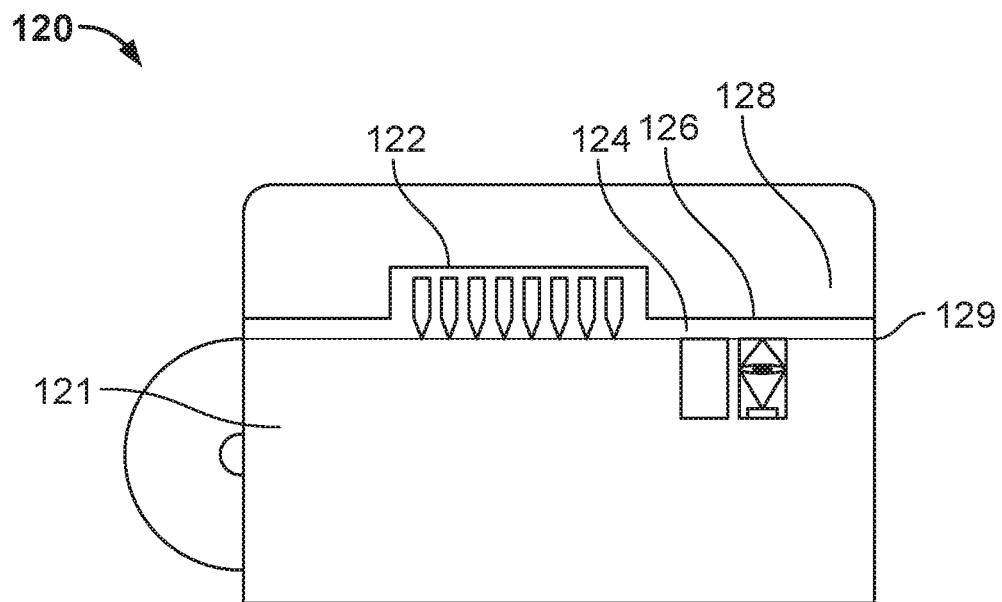
FIG. 2 shows an example of printer subsystem in more detail. The printheads are designed to overprint different components to the same coordinates on the web.

FIG. 2 shows the printer subsystem 120 in more detail. The printer base 121 includes a printer base with a web drive hosting print engine 122, spot imager 126, and spot dryer 128. The print engine prints and over-prints to support the addressing scheme. The print engine 122 may comprise printheads. The printheads are designed to overprint or collocate or overlay different components to the same coordinates on the web 136. A single nozzle, a single printhead, a plurality of nozzles, a plurality of printheads or any combination thereof may overprint components onto the same coordinates. In addition to printheads, the printer may optionally comprise a register 124, a spot imager 126, and a spot dryer 128.

Registration includes spot alignment (if a multi-pass system). The register 124 is intended to maintain alignment between coordinates of the substrate and the printheads. This may be achieved by labeling the substrate with special markings that enable the register to track the motion of the substrate in real-time. In other implementations, the registration may be achieved by dead-reckoning the substrate position from encoders on the rollers. Control of alignment along the web may be done by timing the dispense actions from the print heads. Alignment across the web may require either the substrate or the print heads to move using an actuator.

The spot imager 126 provides verification of component addition. The spot imager 126 may be a camera intended to verify the proper dispense of components or reaction mixtures. To facilitate the function of the spot imager 126, a visible dye may be incorporated into the component inks or reaction mixture.

The spot dryer 128 is intended to desiccate the printed droplets so that they may be dried either in between printheads or upon exiting the printer (for example if the substrate is intended to be rolled upon exiting the printer). Desiccating droplets in between printheads may be useful for preventing liquid from overflowing in a particular coordinate during the over-printing process. Each printhead may dispense a droplet of at least 1 pL, 5 pL, 10 pL, 20 pL, 30 pL, 40 pL, 50 pL, or more. In some implementations, at least 1, 5, 10, 20, 50, 100, or more printheads may dispense into the same coordinate.

The printer subsystem may optionally include a substrate and coating module 129. The substrate and coating module 129 includes web material plus coating/patterning. The substrate may comprise a material or be coated with a material such as a low binding plastic like polyethylene terephthalate (PET) or polypropylene.

Figure 3A:
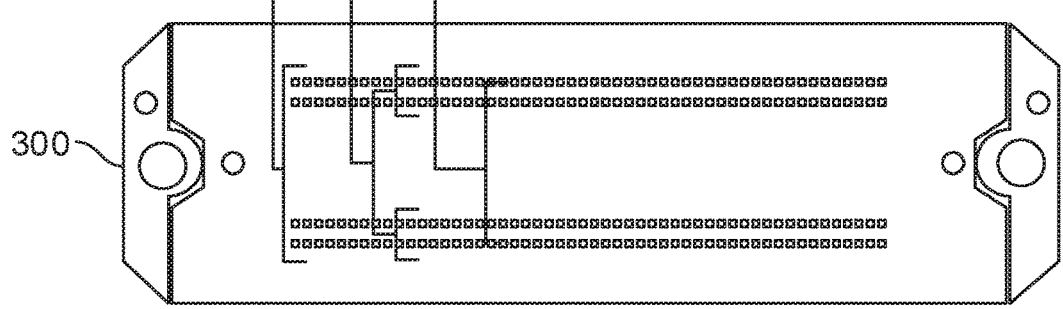
FIGS. 3A-D depict an example of a printhead in the printer.
Figure 3B:
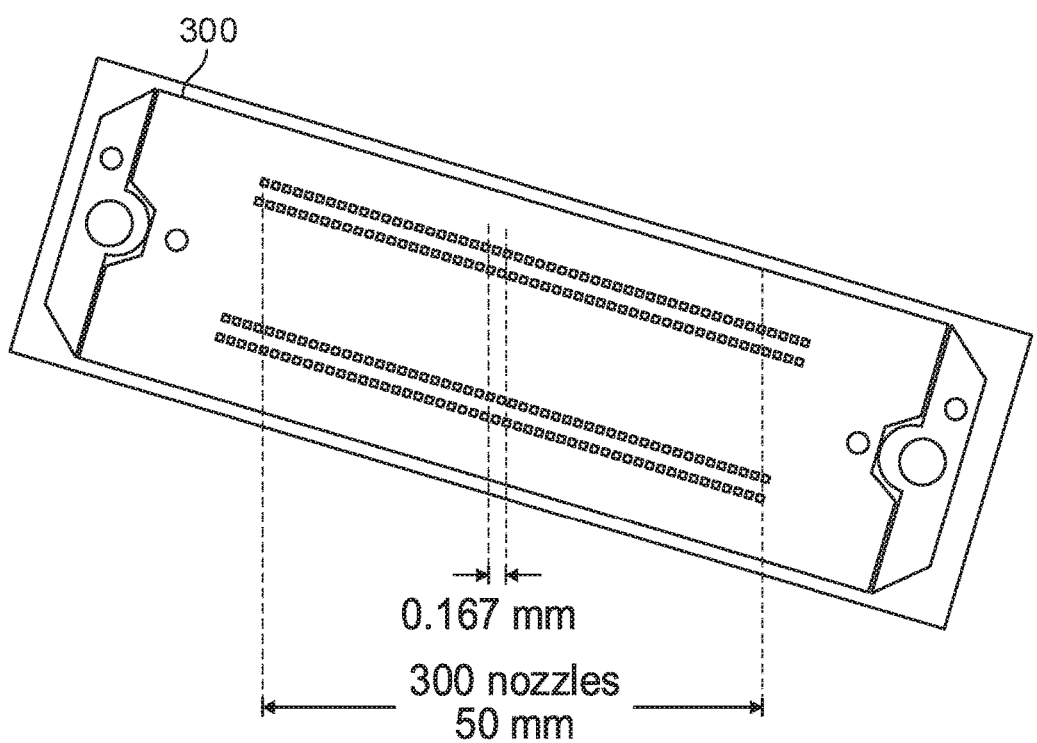
Figure 3C:
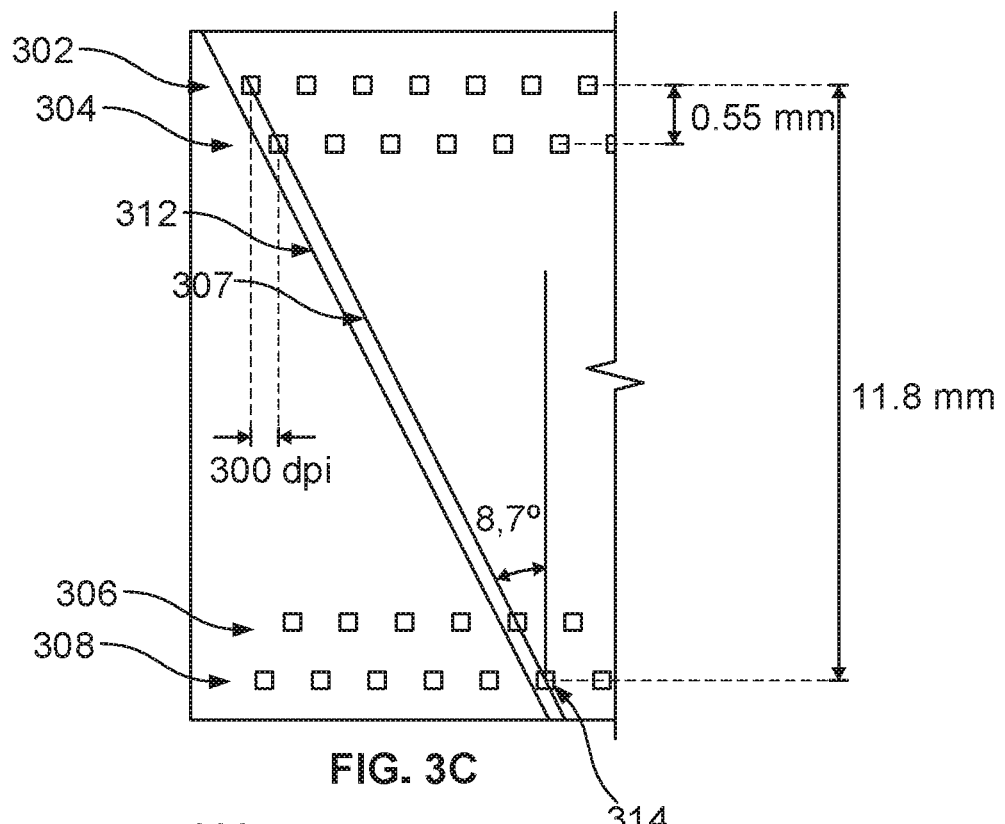
Figure 3D:
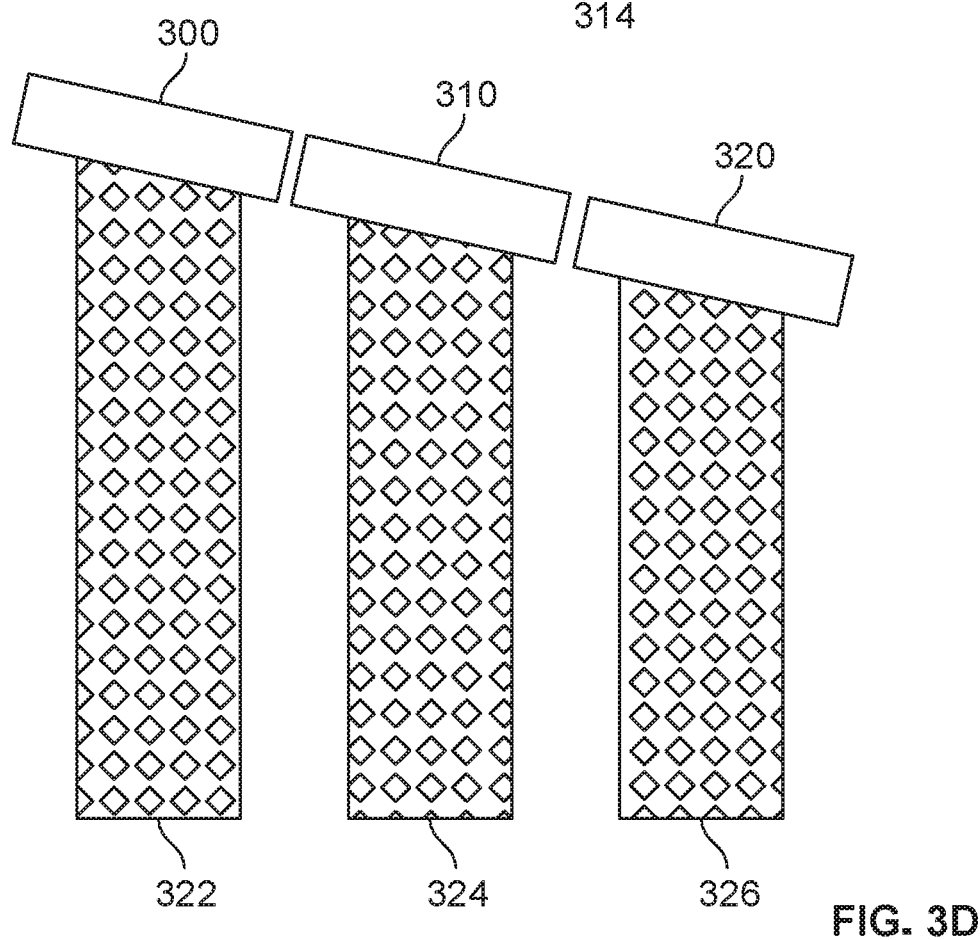

FIG. 3A-D depicts an example of a printhead 300 in a printer (e.g., printer 120 of FIG. 1). A printhead may contain 1, 2, 3, 4, or more inks (distinct component solutions). In this particular example, we consider a printhead 300 that may contain up to 4 inks with one ink provided for each row of nozzles. Additionally printheads may contain multiple nozzles per ink, for example 300 nozzles. In certain instances, the set of web coordinates addressable by some or all nozzles may be disjoint because the nozzles may not be suitably aligned so that each ink may over-print onto the same coordinate of a substrate passing linearly through the printhead. Or, the nozzles for different inks may not be appropriately spaced to print with a desired pitch. To resolve these issues, the printhead may be mounted at an angle (relative to the motion of the web) to enable overprinting of component inks at a desired pitch. As illustrated in FIG. 3B-D, a ~9 degree rotation is sufficient to enable overprinting of 4 inks with 167 um pitch. Specifically, FIG. 3C shows four rows of printerhead nozzles 302, 304, 306, 308. Each of rows 302, 304, 306, 208 may dispense a different component. Substrate 312 (which extends diagonally upward and to the right from the line pointed at by arrow 312) is moved linearly under printhead 300. Because of the 8.7 degree rotation of the printhead, a coordinate 314 on substrate 312 will pass directly beneath nozzles in rows 302, 304, 306, 308 along line 307 such that each nozzle may deposit a component on coordinate 314. As shown in FIG. 3D, multiple printheads 300, 310, 320 may be arranged in parallel to allow for printing on multiple substrates simultaneously. In an example, the printheads may be actuated to bring them into an alignment suitable for over-printing. The printheads may be MEMS (micro-electro-mechanical systems) thin film piezo ink jet heads or MEMS thermal ink jet head. Additives may be added to the component inks to facilitate compatibility with the printheads. For example, solutes like tris may be added to increase conductivity. As an example, humectants or surfactants (e.g. glycerol) may be added to improve ejection quality and printhead nozzle lifetime.

Figure 4:
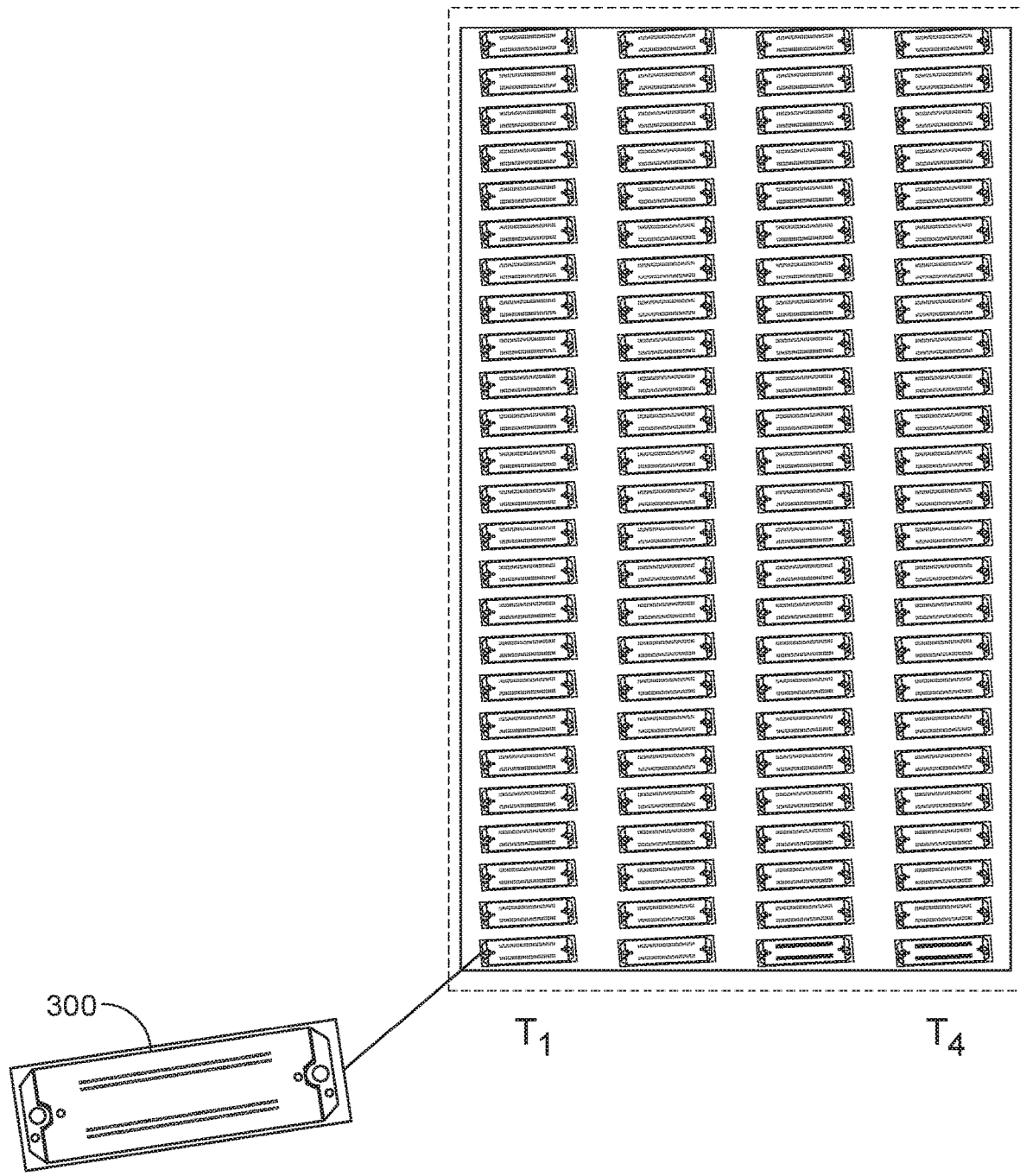
FIG. 4 depicts potential arrangements of the printheads within the printer.

FIG. 4 depicts potential arrangements of the printheads within the printer. It is assumed that the substrate is passing in the longitudinal direction so that printheads on different tracks (T1 through T4) are printing onto independent coordinates, but that printheads along the same track may be printing onto the same coordinates (over-printing) on the substrate. The substrate may be passed through the printer multiple times, each time with new printheads (or the same printheads filled with new inks) in order to receive more DNA components per coordinate. However, if a large enough number of printheads are placed along each track then a single pass may be all that is necessary to incorporate a sufficient number of components for the desired number of identifiers to be built. For example, if identifiers are constructed from the product scheme of 10 layers of 8 components each (enabling $8^{10}$ identifiers, enough to store over a gigabit of data), and each printhead can print 4 components, then mounting 20 printheads along a track can be sufficient to enable all component set collocations in a single pass over the substrate. Multiple tracks may enable more efficient use of the substrate (web), allowing it to be shorter and allowing the identifiers to be built in a more high-throughput manner. If there is more width (latitudinal) in the substrate than there are tracks, then the substrate (or printhead chassis) may be shifted latitudinally after each pass to enable printing onto empty substrate along the width of the substrate instead of along the length. In another embodiment, separate printer base systems may print onto disjoint portions of the same substrate.

Figure 5:
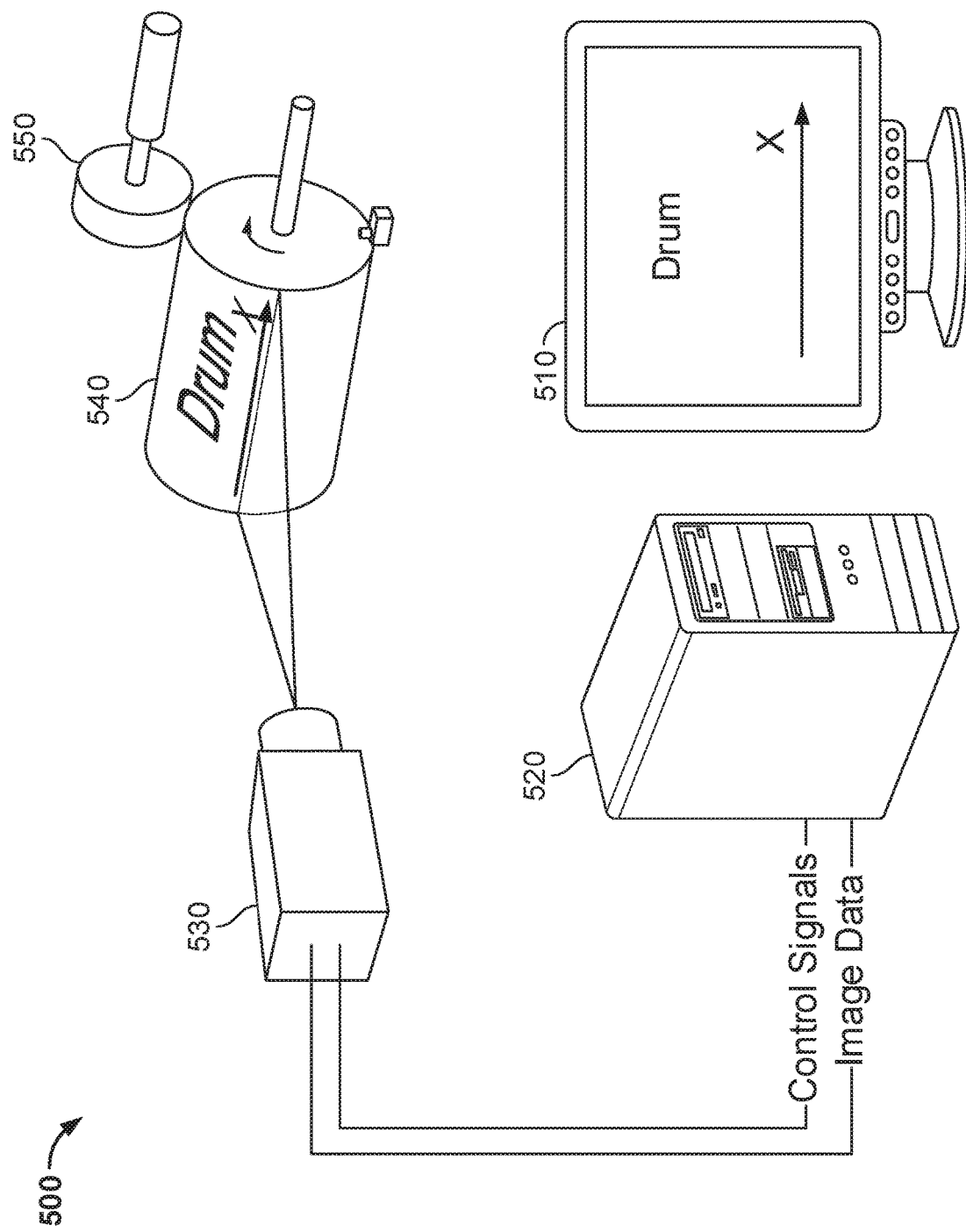
FIG. 5 demonstrates an example set up for the spot imager in the printer subsystem.

FIG. 5 demonstrates an example set up for the spot imager in the printer subsystem. The spot imager may use a line scan inspection principle. For example, the spot imager may include a computer system 520, a display 510, a line scan camera 530, a rotating drum 540, and an encoder 550. Computer system 520 is in communication with line scan camera 530. For example, computer system 520 may send control signals to line scan camera 520 and line scan camera 530 may send image data back to computer system 520. Computer system 520 and line camera system 530 may be communicate via a wireless or wired connection. The image data collected via line scan camera 530 is displayed at display 510. As shown in FIG. 5, line scan camera 530 may capture an image of drum 540 which may then be displayed on display 510.

Figure 6:
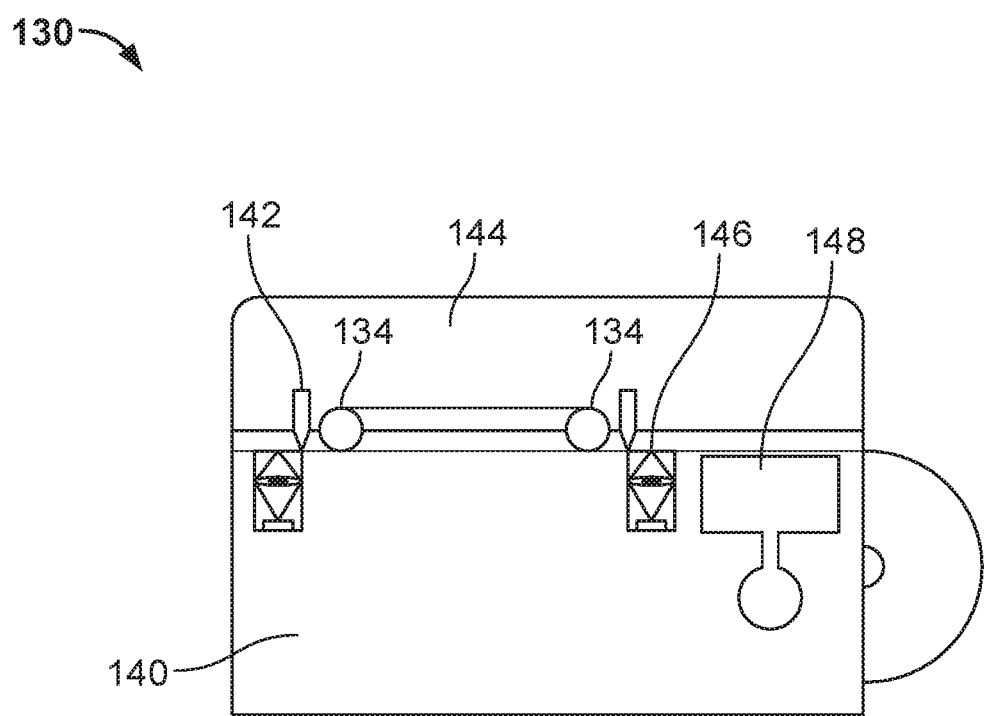
FIG. 6 shows an example of the finisher subsystem in more detail. In addition to a part that dispenses reaction mix onto each coordinate of a substrate, the finisher may also comprise a part that dispenses a reaction inhibitor onto each coordinate of a substrate prior to consolidation.

FIG. 6 shows the finisher subsystem 130 in more detail. Finisher subsystem 130 comprises a finisher base 140 with a web drive, incubation buffer and hosting of dispense, spot humidifier 144, spot imager 146, and pooling subsystem 148. In addition to a part that dispenses reaction mix onto each coordinate of a substrate, the finisher may also comprise a part 142 that dispenses a reaction inhibitor onto each coordinate of a substrate 136 prior to consolidation. These dispensing parts may be printheads. They may be on-demand printheads, but continuous printing may also be sufficient as each coordinate along the web may be expected to receive a dispense. The dispense volume should be sufficient to cover the area of each coordinate where DNA components were previously dispensed. The dispense volume may be at least 1 pL, 5 pL, 10 pL, 20 pL, 30 pL, 40 pL, 50 pL, 60 pL, 70 pL, 80 pL, 90 pL, 100 pL, 150 pL, 200 pL, or more. The printheads may be MEMS (micro-electromechanical systems) thin film piezo ink jet heads or MEMS thermal ink jet head. Additives may be added to the dispensed liquids (e.g. master mix or inhibition mix) to facilitate compatibility with the printheads. For example, solutes like tris may be added to increase conductivity. As another example, humectants or surfactants may be added to improve ejection quality and printhead nozzle lifetime. Further, humectants like glycerol or polyethylene glycol (PEG) may be added to control evaporation both at the nozzle-air interface, as well as after the droplet has been dispensed. These humectants may further benefit the reaction mix by increasing reaction product yield.

Similar to the minter subsystem, the finisher may also comprise a register and a spot imager 146 to align the web with printheads and to validate proper dispensing, respectively. To facilitate the function of the spot imager, a visible dye may be incorporated into the dispensed fluids.

The finisher may further comprise several loops of rollers (configuration of rollers intended to loops the webbing) 134 after the reaction mix dispense so that the reaction on the web (substrate) 136 may incubate for a longer period of time prior to reaction consolidation. The finisher may comprise a fixed internal temperature that is optimal for reaction incubation; for example 4, 12, 25, 37, or more degrees Celsius. To slow control the evaporation of the dispensed reaction mix during the incubation phase, the finisher may comprise a fixed, high humidity level. The humidity level of the finisher subsystem 130 may be controller by spot humidifier 144 that controls maintenance of wet spots through the incubation period (e.g., while the substrate passes over rollers 134).

Lastly, the finisher may comprise a pooling system 148 to consolidate all of the identifier assembly reactions into one container after the incubation. Reaction inhibition may occur prior to this step, or it may occur during this step.

Figure 7:
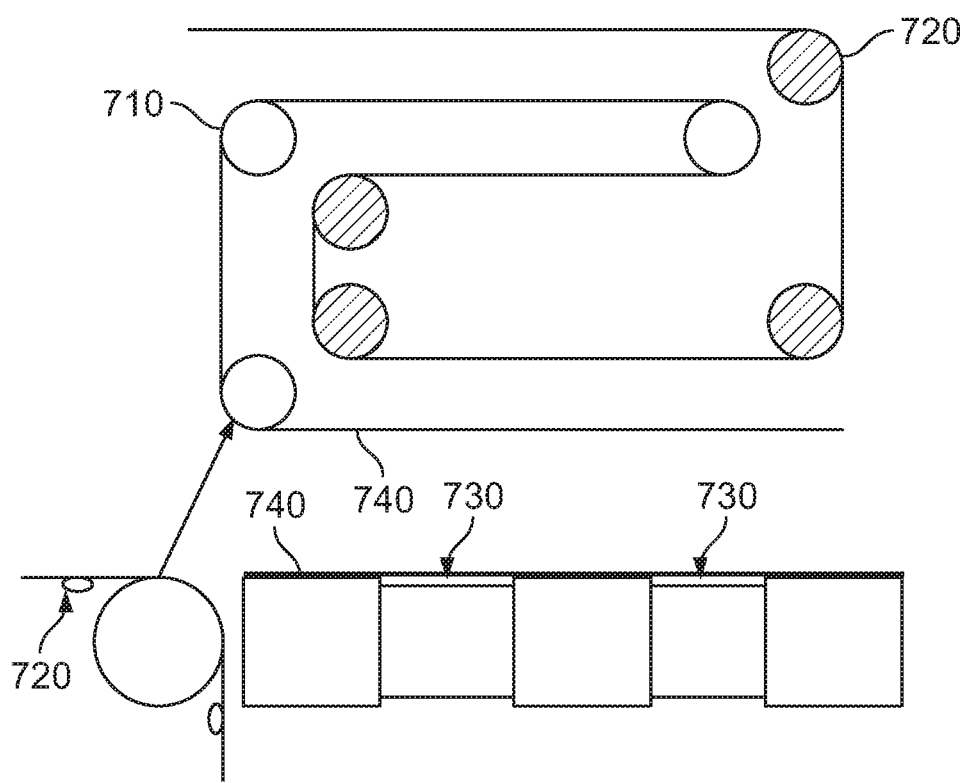
FIG. 7 shows an example of a loop of rollers for passing the web through the finisher during the incubation phase.

FIG. 7 shows an example of a loop of rollers 710, 720 for passing the web through the finisher during the incubation phase. The looping of the web enables longer incubation within a more confined space. For example, if the web is moving through the system at 180 mm/s, then ~60 m of incubated web length is necessary of a 5 minute incubation time, but several loops may enable this length to incubate in a more confined space rather than a linear tunnel of ~60 m. Shorter incubation times may permit shorter incubated web lengths. For example, 45 second incubation times may permit ~9 m of incubated web length and 10 second incubation times may permit ~2 m of incubated web length. At these shorter incubated web lengths, less web loops may be necessary to confine the incubation within a small space.

Because of the geometry of the roller loops, the webbing 740 may pass certain rollers 720 right-side up and other rollers 710 upside down.

The bottom of the figure demonstrates the cross section of a roller 710 along the movement path of the web. The roller may be designed to contain valleys (or grooves, pockets, or any other indentation) 730 between contact points of the substrate 740 so that the reactions (e.g., a coordinates where components were dispensed) may pass through the valley un-interfered. Alternatively the web may be rotated 180 degrees between rollers so that it always passes over the rollers in a right-side up configuration (i.e. 180° twist path). Alternatively the webbing may travel a spiral path through the incubator such that the circular path of the webbing around a set of rollers ensures that the side of the webbing containing reactions does not make contact with the rollers. As an analogy, consider winding a ribbon around a cylinder or applying grip tape to a tennis racquet.

In some implementations, the webbing is recirculating, or continuous, webbing. In some implementations, the webbing is a reel-to-reel system (roller to roller). In some implementations, the webbing follows a snail path. See, e.g., FIG. 7. In some implementations, the webbing follows a spiral path. In some implementations, the webbing follows a 180° twist path. For instance, the webbing will undergo a 180° turn at each roller with the system, wherein the webbing will pass all rollers right-side up configuration.

Figure 8:
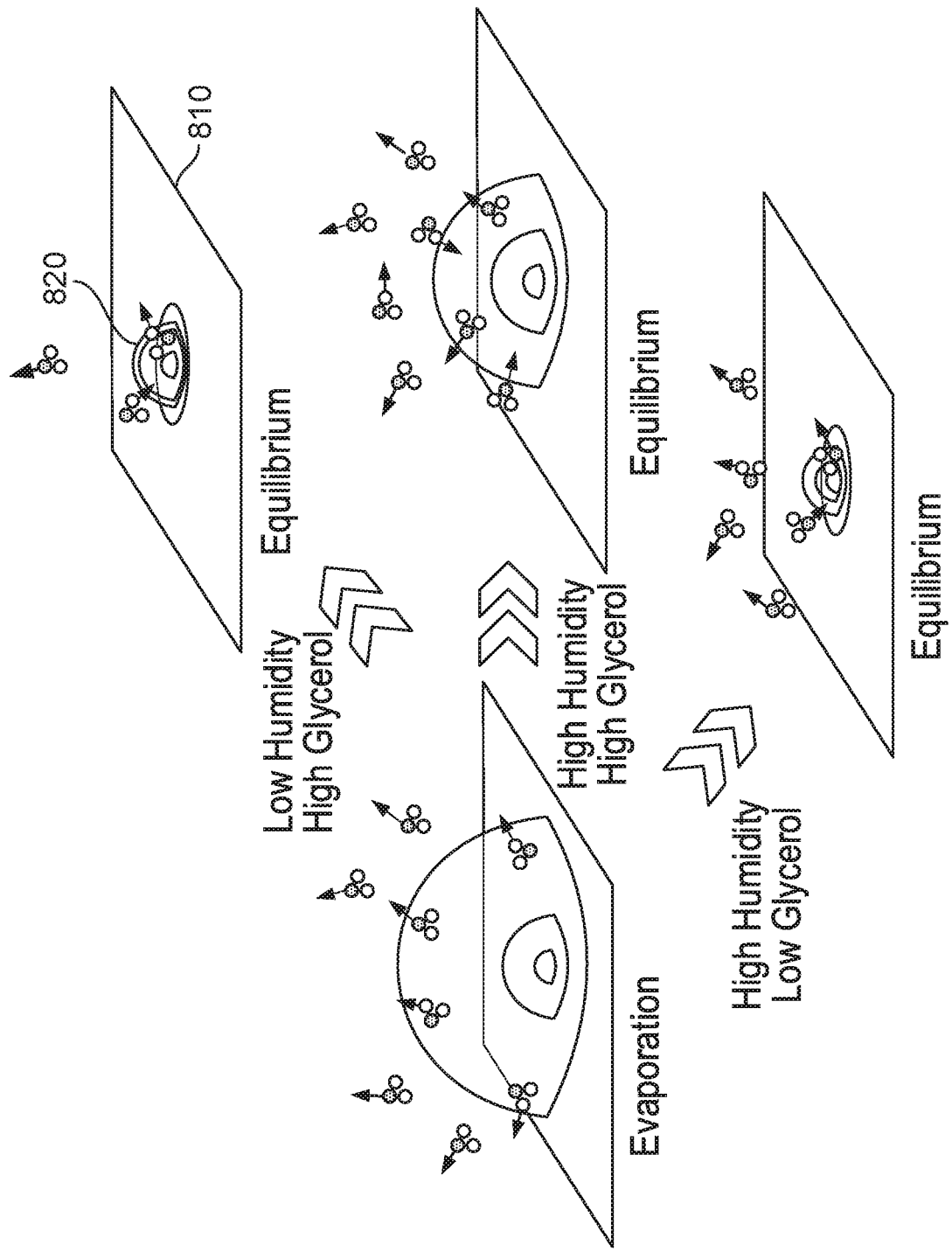
FIG. 8 illustrates the effect of reaction mix glycerol composition and finisher humidity on the anticipated equilibrium volume during incubation.

FIG. 8 illustrates the effect of reaction mix glycerol composition and finisher humidity on the anticipated equilibrium volume during incubation. The particles represent water molecules transitioning between liquid and gaseous phases. The droplet 820 represents a dispensed reaction on the web 810. The outer-shaded region represents water, the middle-shaded region represents glycerol and the inner-shaded region represents solute (e.g. DNA, enzyme/ligase, salt/magnesium, Tris). High humidity and high glycerol conditions will result in an equilibrium reaction composition that is most similar to the original composition. However, changes in reaction composition at equilibrium may be beneficial. For example, an increased relative amount of DNA components may lead to higher production yield of identifiers. Likewise, an increased amount of glycerol content may create a crowding effect that promotes identifier production. Though the reaction efficiency may be negatively affected by increases in certain solute (like salt) concentrations, the initial solute present in the reaction mix may be purposefully under-concentrated and designed to exist at optimal concentration after the reaction droplet evaporates to its equilibrium composition and volume.

Figure 9:
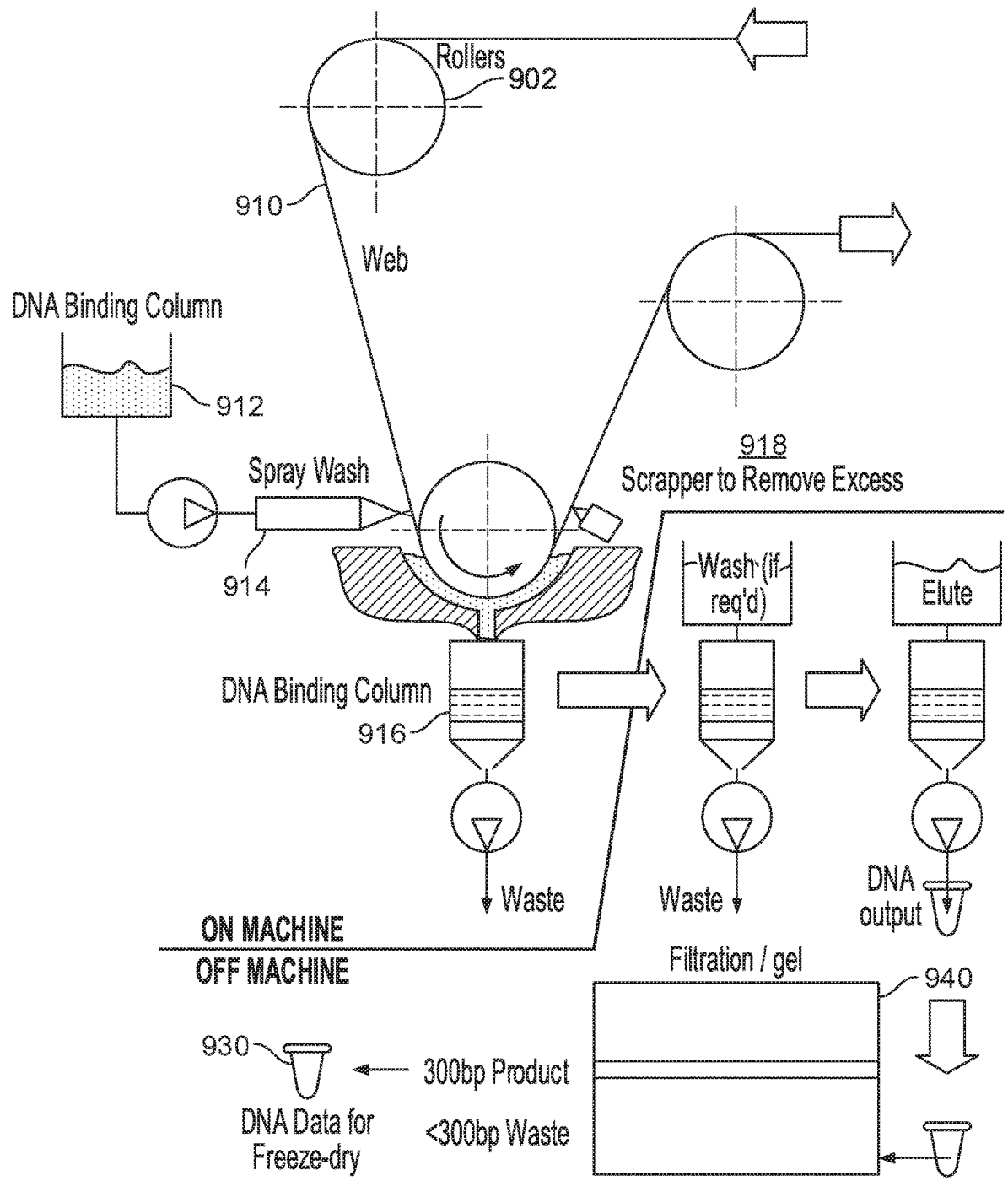
FIG. 9 illustrates an example pooling system that consolidates all reactions from the web into one container.

FIG. 9 illustrates a pooling system that consolidates all reactions from the web into one container. A series of rollers 902 navigates the web 910 through a spray wash 914 and a collection reservoir 942 designed to capture reactions and their identifier products from the web 910. To prevent over-accumulation of volume in this process, the collection fluid may be continuously or iteratively flowed through a membrane designed to capture nucleic acids. For example, the membrane may be a silica membrane and the collection fluid may be DNA binding buffer 912 to facilitate the binding of nucleic acids to the membrane. The collection fluid may further comprise additives to inhibit the reactions so that they do not proceed in the consolidated volume. For example, if the reaction is a ligation reaction, then the collection fluid may contain EDTA (e.g., 25 mM) to chelate Magnesium ion from the ligase and therefore inhibit the reaction. The binding buffer could in one embodiment be recirculated through one or more binding columns to minimize the volume of binding buffer. The web 910 may be wetted with liquid to remove DNA from the web 910 and this may be combined with submerging the web 910 in liquid within the collection reservoir. Agitation of the web 910 or liquid (for example mechanical, fluidic or ultrasonic) and/or heating may be used to promote release of the DNA from the web 910. The scraper 918 could be a physical scraper, a liquid jet or a gas (e.g. air) jet, again to aid removal of DNA from the web 910. One or more sprays could be used to aid release of DNA from the web 910.

After the DNA is captured on the membrane, it may be removed from the system (machine) for elution and further evaluation. Further evaluation may comprise running the DNA on a gel and selecting for the band size corresponding to the expected identifier length (thereby purifying identifiers from other potential off-target products). In this example, the target identifier length is 300 bp. The DNA output may optionally be passed through a gel or other filtration 940 resulting in DNA data 930 that may be freeze dried.

Instead of reaction mix being added and inhibited prior to or during pooling, there is another embodiment of this system in which the reaction occurs in the pooling step. In this embodiment, components are annealed but not assembled during the incubation process, and then they are consolidated together in the pool which contains the reaction mix and proper environment conditions (e.g. temperature, pH, salts) for component assembly into identifiers. This embodiment may enable shorter incubation time on the web 910 and less stringent hardware requirements in the finisher, as once the annealed components are pooled, the rest of the reaction may proceed outside of the system (machine). In this embodiment, in order to prevent unwanted cross-assembly between components of different identifiers in the pooled reaction, special care may be taken to ensure that components are strongly annealed to each other prior to and during the pooling. This may involve using components with long sticky ends (and hybridization regions) for strong annealing as well as using lower temperatures in the pooling step to maintain annealed products and to restrict diffusion of un-annealed products.

Figure 10:
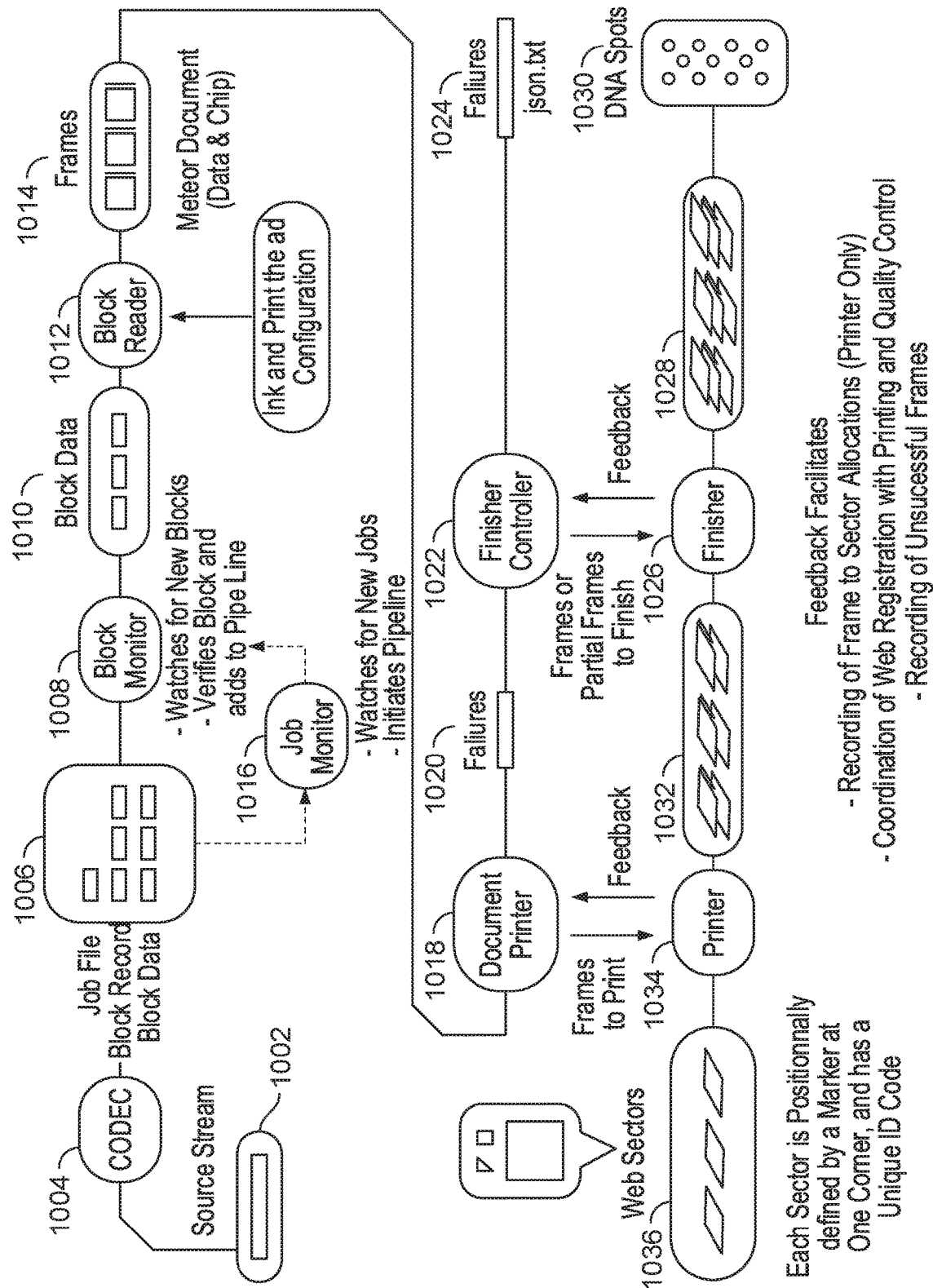
FIG. 10 depicts a schematic of an embodiment of the data transfer pipeline through the PFS.

FIG. 10 depicts a schematic of an embodiment of the data transfer pipeline through the PFS. FIG. 10 starts at source stream 1002 which contains 1 Tb of data. Source stream 1002 is transferred to codec 1004 and fed into job module 1006. Job module 1006 creates a job file, a block record, and block data for each source stream and/or codec file. This information is fed to block monitor 1008. Job module 1006 is monitored by job monitor 1016 which communicates with block monitor 1008. Block monitor 1008 watched for new blocks, verifies blocks and adds them to the pipeline for printing. The block data 1010 from job module 1006 is separated out and sent to block reader 1012 which processes the necessary ink and printhead configuration to print the block data. The block data is then transformed to printable frames 1014 that include the block data 1010 and "chirps" configured to test the accuracy of the data transfer. The frames 1014 are then sent to document printer module 1018 that communicates with printer 1034. For example, document printer module 1018 sends frames 1014 to printer 1034 to print and printer 1034 sends feedback to document printer 1018. Any failures 1020 are communicated to finish controller 1022 which are written to a text file or other storage method 1024. In additional to electronically communicating with document printer 1018, the printer 1034 receives the physical web sectors 1036. The web sectors 1036 are positionally verified by markers at one corner. Each webs sector has a unique ID code. Printer 1032 deposits components 1032 onto the web. The web then continues to the finisher 1026. Finisher 1026 communicates with finish controller 1022. Finish controller 1022 sends information regarding frames or partial frames to finish to finisher 1026 and finisher 1026 sends feedback back to finish controller 1022. Feedback from both the printer and finisher systems 1034, 1026 facilitates recording of the frame to sector allocating, coordination of web registration with printing and quality control, and recording of unsuccessful frames. After leaving the finisher 1026, the web has been printed and finished 1028 resulting in a substrate with DNA spots 1030 that may then be sent to a polling system or any other suitable storage method.

Figure 11:
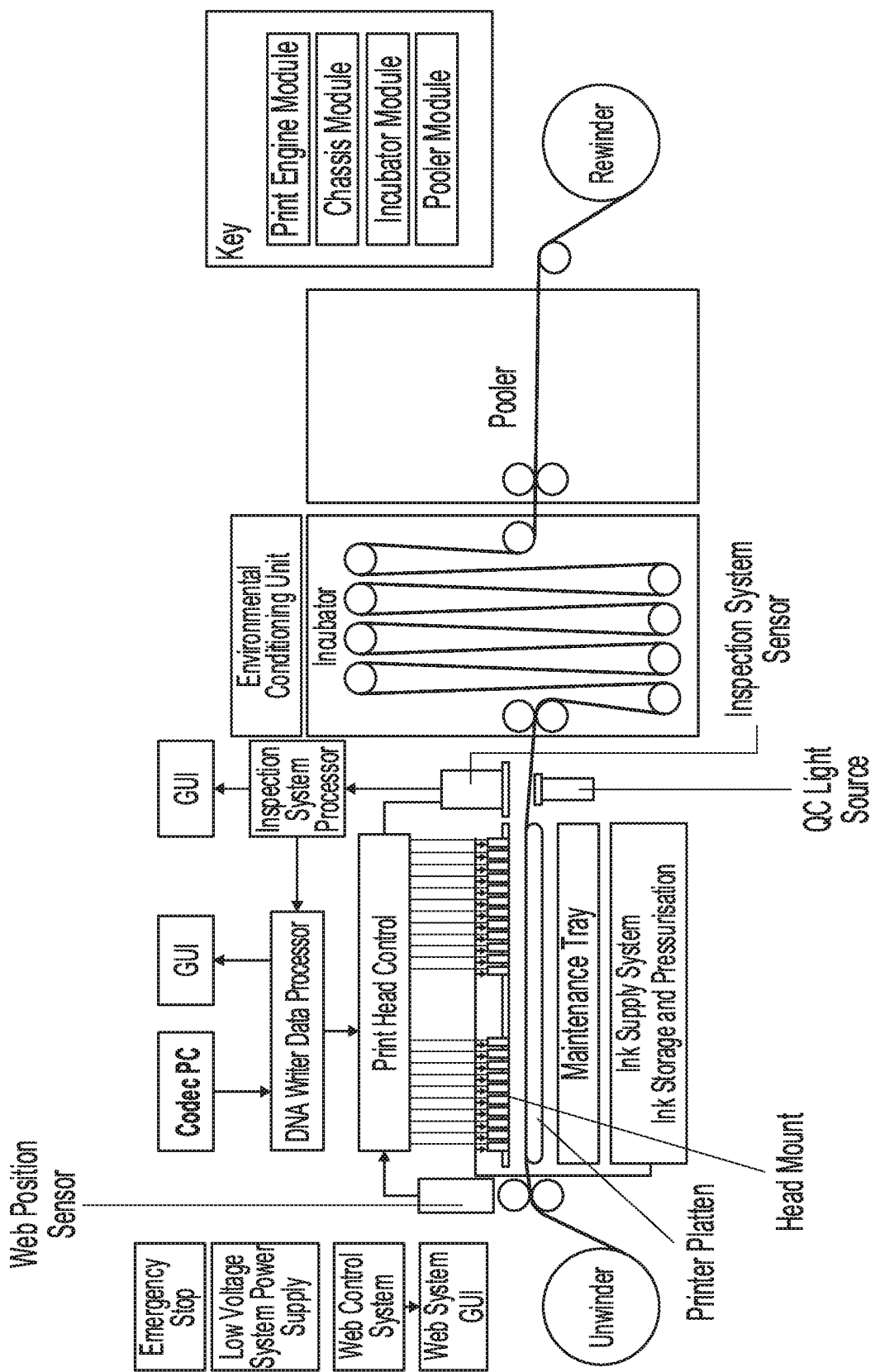
FIG. 11 illustrates an embodiment of the PFS that comprises four modules: a chassis module, a print engine module, an incubator module, and a pooling module.

FIG. 11 illustrates an embodiment of the PFS that comprises four modules: a chassis module, a print engine module, an incubator module, and a pooling module. The function of the chassis module may be to provide a base system that drives, stabilizes, and controls the movement of webbing through all modules of the system. The function of the print engine module may be to print DNA components as well as other materials and reagents into reaction droplets on the webbing. The function of the incubator module may be to provide time and environmental control for improved product (e.g., assembled DNA or identifier) yield in the reaction droplets. The function of the pooler module may be to remove reaction droplets from the webbing and consolidate them into one container.

In some embodiments, the reaction droplets may assemble DNA identifiers through enzymatic ligation. In some embodiments, the reaction droplets may assemble DNA identifiers through click chemistry.

In some embodiments, the incubator module may comprise 100, 50, 10, 5, 1, or 0.1 meters of webbing or less. In some embodiments, the PFS may not have an incubator module.

In some embodiments, the print engine or incubator may contain intermittent printheads or dispensing submodules to replenish volume in the reaction droplets as they evaporate on the webbing.

In some embodiments, the webbing passing through the PFS may unwind from a roll prior to the print engine and re-wind on a roll after the pooler. In some embodiments, the webbing may form a continuous loop that passes back to the print engine after the pooler.

Figure 12:
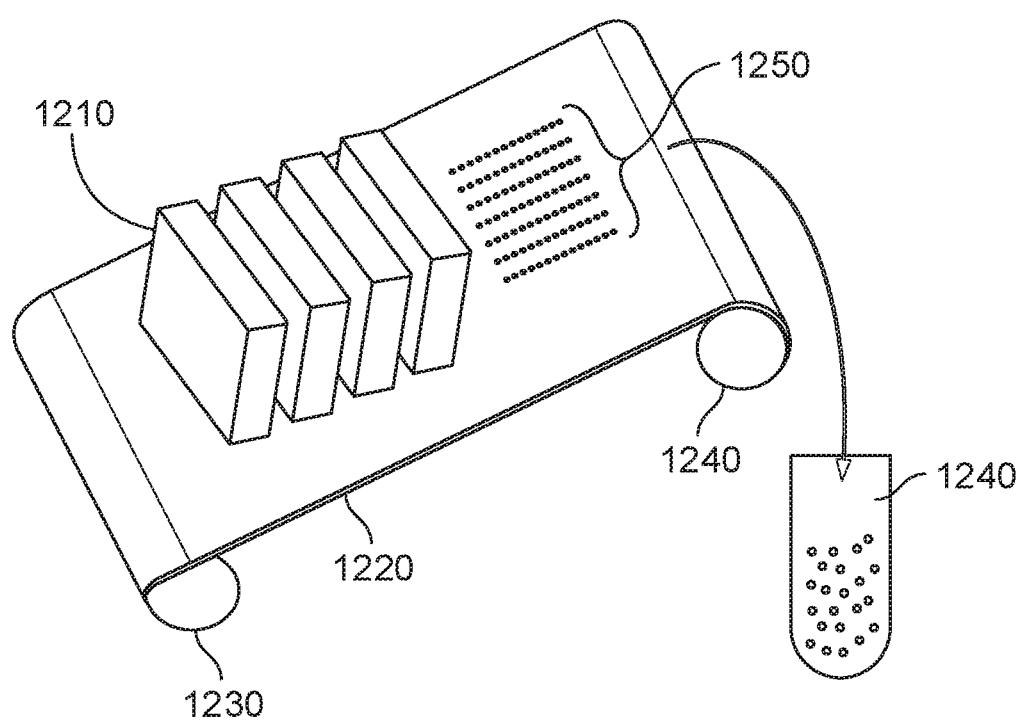
FIG. 12 illustrates an embodiment of the PFS that pools reaction droplets into an emulsion.

FIG. 12 illustrates an embodiment of the PFS that pools reaction droplets into an emulsion 1260. The emulsion 1260 may comprise oil or any liquid that is not miscible with the reaction droplets, thereby enabling the reaction droplets 1250 to maintain their contents, even after being pooled. The webbing 1220 of PFS may be coated with oil prior to passing underneath the printheads 1210 (e.g. via rollers 1230 and 1240). The reaction droplets 1250 may contain surfactants and other additives to control their size and shape in the emulsion. The surfactants and additives may also promote stability within the emulsion and prevent coalescence between different reaction droplets. The pooled emulsified reaction droplets may be passed through a microfluidic device. The pooled emulsified reaction droplets may be incubated. Moreover, the pooled emulsified reaction droplets may be aggregated and isolated from the emulsion.

Figure 13:
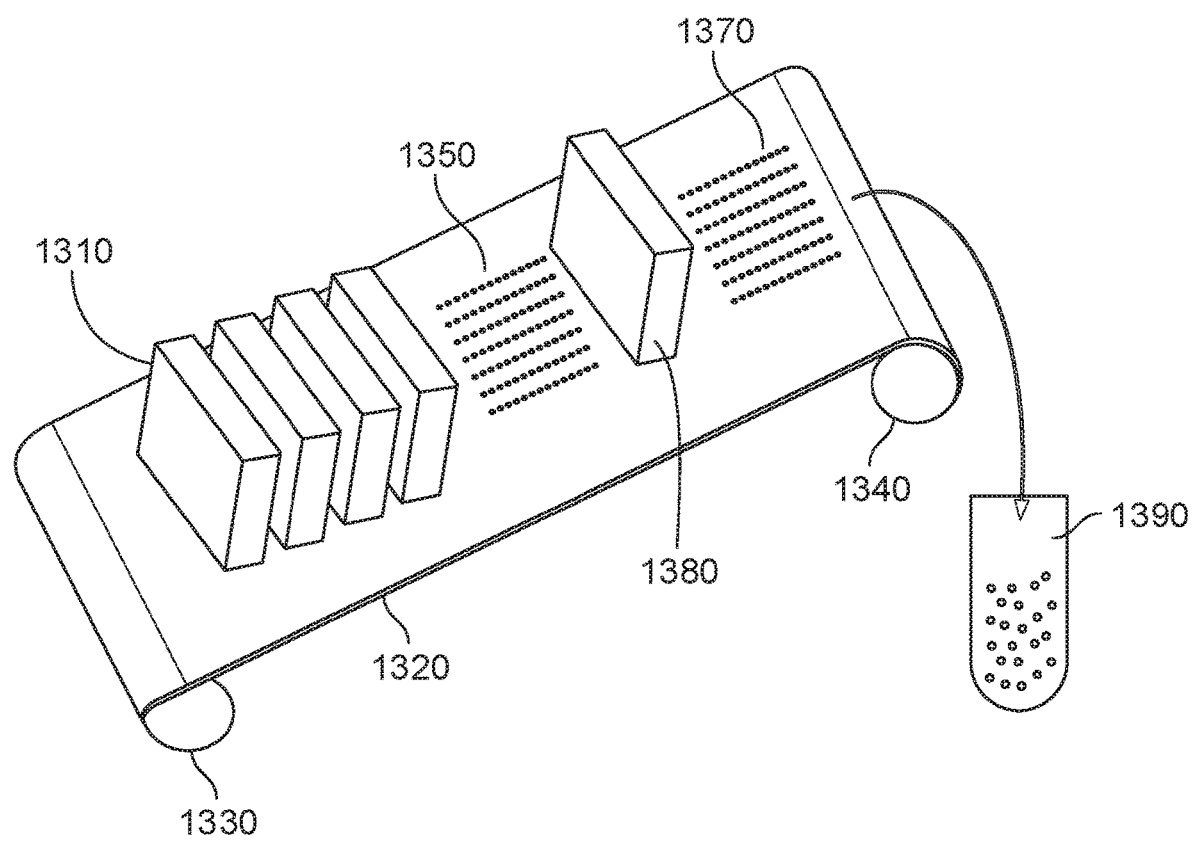
FIG. 13 illustrates an embodiment of the PFS where reaction droplets are coated with oil (or another non-miscible liquid) after being printed onto the webbing.

FIG. 13 illustrates an embodiment of the PFS where reaction droplets 1350 are coated with oil (or another non-miscible liquid) 1370 after being printed onto the webbing 1320. The oil coating may occur with an oil dispense submodule 1380 that prints, dispenses, or sprays the oil on the reaction droplets 1350 as the webbing 1320 passes under printhead cluster 1310 via rollers 1330 and 1340. The oil may lessen or prevent evaporation of the reaction droplets on the webbing 1320. The reaction droplets may contain surfactants and other additives. The oil-covered reaction droplets 1370 may be pooled into an emulsion 1390. The pooled emulsified reaction droplets may be passed through a microfluidic device. The pooled emulsified reaction droplets may be incubated. Moreover, the pooled emulsified reaction droplets may be aggregated and isolated from the emulsion.

Figure 14:
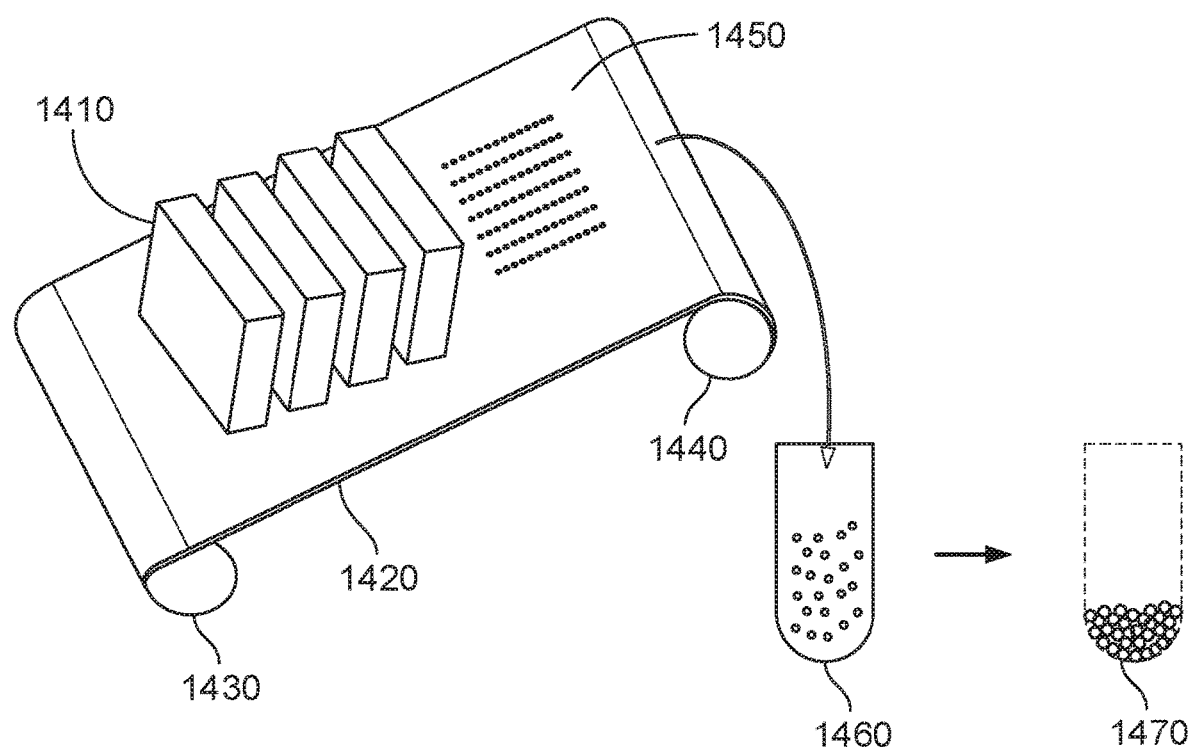
FIG. 14 illustrates an embodiment of the PFS where reaction droplets contain beads that bind the printed DNA components.

FIG. 14 illustrates an embodiment of the PFS where reaction droplets 1450 contain beads that bind the printed DNA components. The beads may be coated with silica, carboxyl groups, or amine or imidazole moieties that bind DNA. Alternatively or in addition, the beads may be coated with streptavidin that binds DNA components through a biotin linkage. The biotin may be linked to DNA components with a photo- or UV-cleavable linker.

The webbing 1420 may be ubiquitously covered with beads or patterned with beads prior to passing underneath the printheads 1410 (e.g., via rollers 1430 and 1440). Alternatively, or in addition, the beads may be deposited or printed into each of the reaction droplets 1450. The reaction droplets may contain additives that promote DNA binding to the beads. The beads may be at a quantity of 1, 2, 3, 5, 10, 20, 50, 100 or more per reaction droplet.

The reaction droplets 1450 may be pooled in a solution 1460 that prevents further association of DNA to the beads. The solution 1460 may contain blocking agents such as BSA. The DNA-bound beads in the pooled solution may be separated from the solution and dried 1470. Separation may occur through centrifugation. In another embodiment, the beads may be magnetic and they may be separated with a magnet.

Pooled DNA-bound beads (dried 1470 or in solution 1460) may be further encapsulated in emulsified reaction droplets. In one embodiment, DNA-bound beads are each encapsulated in a reaction droplet using microfluidics. In another embodiment, DNA-bound beads are each encapsulated in a reaction droplet by mixing the reaction solution and oil (or another immiscible liquid) such that droplets spontaneously form. The ratio of spontaneously formed reaction droplets to DNA-bound beads may be tuned such that no reaction droplet is likely to contain more than one DNA-bound bead. The reaction droplets may contain surfactants or other additives to control their size or to prevent coalescence of other reaction droplets.

Reaction droplets may contain reagents that disassociate the DNA on the beads. The reaction droplets may contain reagents that ligate the DNA components together to form identifiers. The reaction droplets may contain enzymatic ligases as well as ligation co-factors such as ATP, DTT, or salts.

If DNA is bound to the beads through a photo-cleavable or UV-cleavable linkage, the DNA may be released from the beads by exposing the emulsion to electromagnetic waves of the appropriate wavelength (e.g. light or UV).

Figure 15:
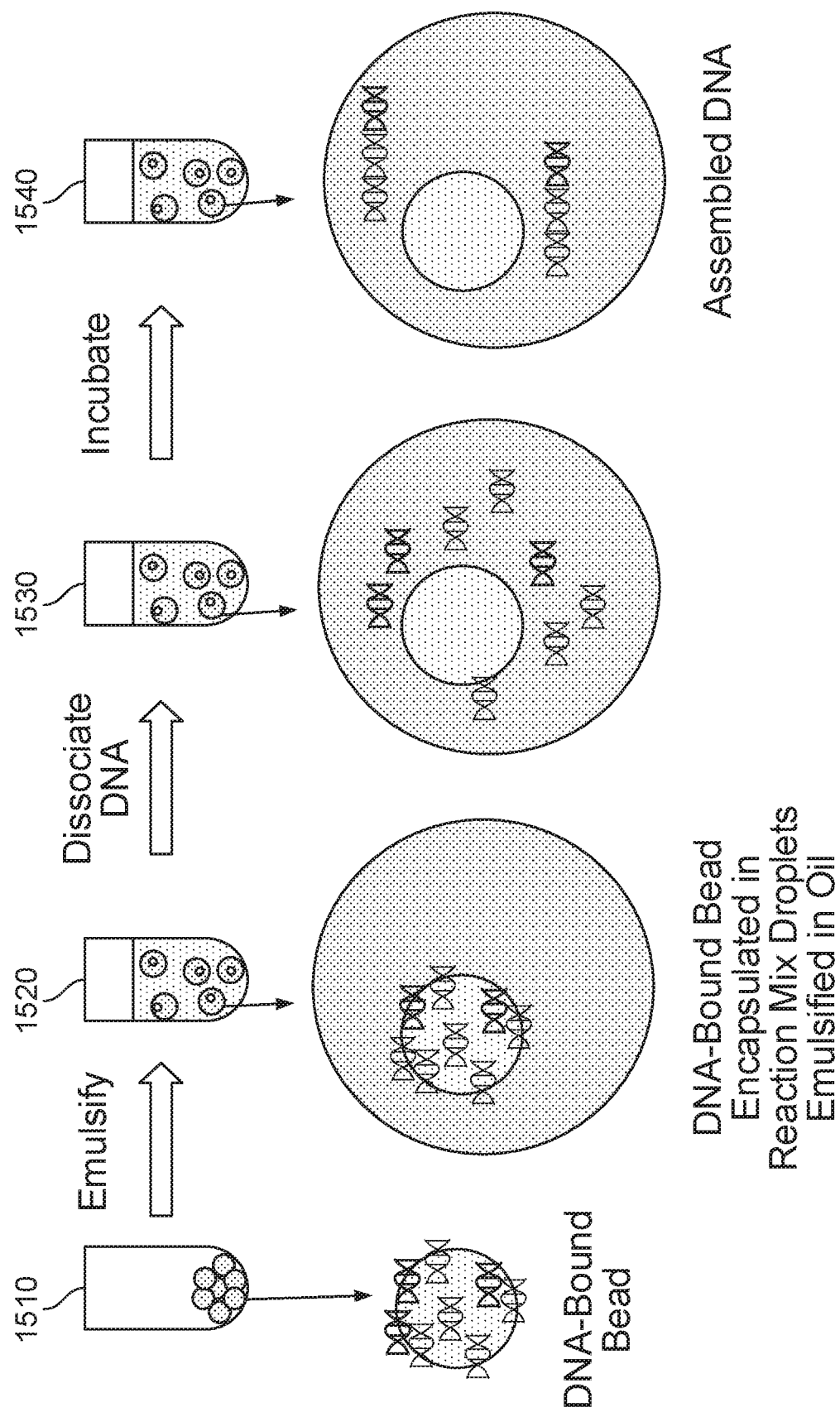
FIG. 15 illustrates an example of how DNA components bound onto beads may be processed into identifiers using an emulsion.

FIG. 15 illustrates an example of how DNA components bound onto beads may be processed into identifiers using an emulsion. At step 1510 DNA-bound beads are provided. The DNA-bound beans are then emulsified at 1520 such that the DNA-bound beads encapsulated in reaction mix droplets are immersed in oil. The DNA is then dissociated resulting in mixture 1530. The dissociated DNA mixture is incubated, resulting in the assembled DNA of 1540.

While exemplary implementations have been shown and described herein, it will be obvious to those skilled in the art that such implementations are provided by way of example only. Numerous variations, changes, and substitutions will occur to those skilled in the art. It should be understood that various alternatives to the implementations described herein may be employed.

Example Modifications to Decrease the PFS Size

As previously described in FIG. 11, the PFS may comprise four modules: chassis, print engine, incubator, and pooler. For the PFS that encodes 1 Tb of information in DNA, the approximate size of each module may be as listed in the to table below:

TABLE 1

| | Approximate module size | | |
|---|---|---|---|
| Module | L (mm) | W (mm) | H (mm) |
| Printer | 1850 | 1200 | 2000 |
| Incubator | 2300 | 1150 | 2000 |
| Chassis | 800 | 1150 | 2000 |
| Pooler | 600 | 1150 | 1600 |

To decrease the size of the PFS, one may reduce the size of the individual modules or remove modules. Examples of modification to decrease size may include the following:

(1) Increasing print head capacity in the print engine. Either custom printheads or additional print heads may be used to allow for the number of nozzle columns to triple (or increase by a larger factor). This may triple the number of printed reactions as well as the print width on the webbing.

(2) Using recirculating webbing. For example, the PFS may use 21 kilometers of polypropylene webbing to print enough reactions to encode 1 Tb of information. To eliminate the use of webbing reels (or rolls), recirculating webbing may be used as an alternative to roll-to-roll webbing. Recovery studies show that DNA can be readily removed from the web in the pooler.

(3) Decreasing ligation reaction time. This may facilitate the use of a smaller incubator or no incubator at all. To decrease ligation reaction time without sacrificing yield, the chemistry can be optimized to meet a higher ligation rate.

(4) Performing ligation temperature and ambient conditions. This may eliminate the need for an incubator module.

(5) Using oil emulsions to maintain reaction droplet volume or to enable ligation to start or continue after the pooler. This may eliminate the need for an incubator module.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed.

Applications of Methods and Systems of Combinatorial DNA Assembly

The methods and systems described herein for combinatorial assembly of components into large defined sets of identifiers have been described thus far as they relate to information technology (for example, data storage, computing, and cryptography). However, these systems and methods may more generally be used for any application of high throughput combinatorial DNA assembly.

In one embodiment, we may create a library of combinatorial DNA that encodes for amino acid chains. Those amino acid chains may represent either peptides or proteins. The DNA fragments for assembly may comprise codon sequences. The junctions along which fragments assemble may be functionally or structurally inert codons that will be common to all members of the combinatorial library. Alternatively, the junctions along which fragments assemble may be introns that are eventually removed from messenger RNA which is later translated into the processed peptide chain. Certain fragments may not be codons, but rather barcode sequences that (in combination with other assembled barcodes) uniquely tag each combinatorial string of codons. The assembled products (barcodes+string of codons) may be pooled together and encapsulated in droplets for in vitro expression assays, or pooled together and transformed into cells for in vivo expression assays. The assays may have a fluorescent output such that the droplets cells may be sorted into bins by fluorescent strength and subsequently their DNA barcodes sequenced for the purpose of correlating each codon string with a particular output.

In another embodiment, we may create a library of combinatorial DNA that encodes for RNAs. For example, the assembled DNA may represent combinations of microRNAs or CRISPR gRNAs. Either pooled in vitro or in vivo RNA expression assays may be performed as described above with either droplets or cells, and with barcodes to keep track of which droplets or cells contain which RNA sequence. However, some pooled assays may be done outside droplets or cells if the output itself is RNA sequencing data. Examples of such pooled assays include RNA aptamer screening and testing (for example, SELEX).

In another embodiment, we may create a library of combinatorial DNA that encodes for genes in a metabolic pathway. Each DNA fragment may contain a gene expression construct. The junctions along which fragments are assembled may represent inert DNA sequences in between genes. Either pooled in vitro or in vivo gene pathway expression assays may be performed as described above with either droplets or cells, and with barcodes to keep track of which droplets or cells contain which gene pathways.

In another embodiment, we may create a library of combinatorial DNA with different combinations of gene regulatory elements. Examples of gene regulatory elements include 5' untranslated regions (UTRs), ribosome binding sites (RBSs), introns, exons, promoters, terminators, and transcription factor (TF) binding sites. Either pooled in vitro or in vivo gene expression assays may be performed as described above with either droplets or cells, and with barcodes to keep track of which droplets or cells contain which genetic regulatory constructs.

In another embodiment, a library of combinatorial DNA aptamers may be created. Assays can be performed to test the ability of the DNA aptamers to bind ligands.

What is claimed is:

1. A method for assembling an identifier nucleic acid molecule, the method comprising:
    dispensing a first droplet of a first solution comprising a first component nucleic acid molecule onto a coordinate on a substrate using a first printhead of a printer-finisher system;
    dispensing a second droplet of a second solution comprising a second component nucleic acid molecule onto the coordinate on the substrate using a second printhead of the system, such that the first and second component nucleic acid molecules are collocated on the substrate; and
    linking the first and second component nucleic acid molecules to form the identifier nucleic acid molecule using a finisher of the system, the identifier nucleic acid molecule representing a position of a symbol in a string of symbols of digital information, wherein the linking is performed by dispensing a reaction mix onto the coordinate on the substrate, providing a condition necessary to link the first and second component nucleic acid molecules, or both.

2. The method of claim 1, wherein the finisher comprises a third printhead, which dispenses the reaction mix.

3. The method of claim 1, wherein the finisher comprises an incubator, and wherein linking the first and second component nucleic acid molecules comprises:
    incubating the coordinate using the incubator.

4. The method of claim 3, wherein incubating comprises subjecting the coordinate to at least one of a fixed temperature or a fixed humidity level.

5. The method of claim 1, further comprising:
    using a roller system, moving the substrate past the first printhead, the second printhead, and the finisher.

6. The method of claim 5, wherein the roller system comprises at least one roller that moves the substrate in a linear direction.

7. The method of claim 6, wherein the substrate comprises a continuous loop of a material, and wherein the at least one roller is part of a set of rollers in the roller system that causes the coordinate on the substrate to pass the first printhead, the second printhead, and the finisher multiple times.

8. The method of claim 7, wherein the substrate comprises a first surface and a second surface opposite the first surface, such that the first and second droplets are dispensed on the first surface, and the roller system contacts the second surface.

9. The method of claim 1, wherein the first printhead comprises a first plurality of nozzles configured to dispense droplets of the first solution at different coordinates on the substrate.

10. The method of claim 9, wherein the second printhead comprises a second plurality of nozzles configured to dispense droplets of the second solution at different coordinates on the substrate.

11. The method of claim 1, wherein the first and second printheads are each a MEMS thin-film piezo ink jet head or a MEMS thermal ink jet head.

12. The method of claim 1, wherein the finisher comprises a pooling system, and wherein the method further comprises:
    capturing the identifier nucleic acid molecule in a container using the pooling system.

13. The method of claim 12, wherein the captured identifier nucleic acid molecule is pooled with additional identifier nucleic acid molecules in a pooling solution in the container.

14. The method of claim 13, wherein the pooling solution comprises a reaction inhibitor.

15. The method of claim 13, wherein the pooled identifier nucleic acid molecules and the pooling solution form an emulsion in the container.

16. The method of claim 12, wherein capturing comprises collecting fluid from the substrate using a membrane.

17. The method of claim 12, wherein capturing comprises scraping fluid from the substrate using a scraper.

18. The method of claim 1, wherein the finisher further comprises a heater and the reaction mix comprises PCR reagents, and wherein the method further comprises:
    heating coordinate using the heater in a cycle of temperatures, such that the identifier nucleic acid molecule is amplified via PCR.

19. The method of claim 1, wherein the first and second printheads are mounted within the system at an angle relative to motion of the substrate, such that the first and second printheads are configured to overprint on the coordinate.

* * * * *